United States Patent
Murao et al.

(10) Patent No.: US 7,057,066 B2
(45) Date of Patent: Jun. 6, 2006

(54) PROCESS FOR PRODUCING 3-AMINO-2-HYDROXYPROPIONIC ACID DERIVATIVES

(75) Inventors: Hiroshi Murao, Hyogo (JP); Koki Yamashita, Kobe (JP); Toshihiro Takeda, Takasago (JP); Yasuyoshi Ueda, Himeji (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 10/312,208

(22) PCT Filed: Jun. 26, 2001

(86) PCT No.: PCT/JP01/05440

§ 371 (c)(1),
(2), (4) Date: Jan. 28, 2003

(87) PCT Pub. No.: WO02/00601

PCT Pub. Date: Jan. 3, 2002

(65) Prior Publication Data

US 2004/0049074 A1    Mar. 11, 2004

(30) Foreign Application Priority Data

Jun. 26, 2000  (JP) .......................... 2000-190949
May 23, 2001  (JP) .......................... 2001-154074

(51) Int. Cl.
  *C07C 229/06*   (2006.01)
  *C07C 229/34*   (2006.01)

(52) U.S. Cl. ............... 562/444; 562/433; 562/441; 562/443; 562/452; 562/457; 562/553; 562/567; 560/160

(58) Field of Classification Search ............ 562/443, 562/441, 457, 553, 444, 452, 567, 433; 560/160
See application file for complete search history.

(56) References Cited

U.S. PATENT DOCUMENTS 4,294,966 A    10/1981  Zergenyi
4,296,242 A *  10/1981  Nagabhushan et al. ..... 560/160

FOREIGN PATENT DOCUMENTS

| EP | 156279 A2 | 10/1985 |
| EP | 435068 A2 | 7/1991 |
| EP | 0 885 879 A1 | 12/1998 |
| EP | 930292 A1 | 7/1999 |
| JP | 32-1323 B1 | 2/1957 |
| JP | 32-002675 * | 5/1957 |
| JP | 32-2675 B1 | 5/1957 |
| JP | 36-21317 B1 | 11/1961 |
| JP | 37-4310 B1 | 6/1962 |
| JP | 58-35152 A | 3/1983 |

(Continued)

OTHER PUBLICATIONS

Beresford, Kenneth J. M. et al., "Versatile Synthesis of L-α-Amino Acids Stereospecifically Labelled on the β-Carbon Atom", TETRAHEDRON, vol. 52, No. 29, Jul. 1996, pp. 9891-9900.

(Continued)

*Primary Examiner*—Rosalynd Keys
(74) *Attorney, Agent, or Firm*—Foley & Lardner LLP

(57) ABSTRACT

The present invention provides a process for preparing 3-amino-2-hydroxypropionic acid derivatives (1) which does not use dangerous reagents, is economically advantageous, and is suitable for an industrial production, which process comprises:

treating N-protected-3-amino-2-hydroxypropionic acid derivatives (2) having a steric configuration at 2-position carbon reverse to that of derivatives (1) with a leaving group-introducing agent to convert into N-protected-3-aminopropionic acid derivatives (3), then treating the derivatives with a basic substance to convert into substituted-3-amino-2-hydroxypropionic acid derivatives (4) having an inverted steric configuration at 2-position carbon, and then converting the derivatives into 3-amino-2-hydroxypropionic acid derivatives (1).

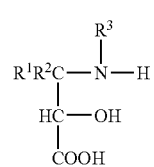

(1)

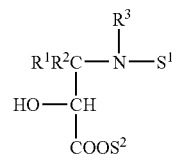

(2)

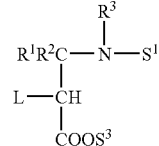

(3)

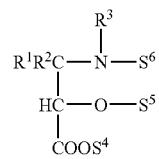

(4)

33 Claims, No Drawings

FOREIGN PATENT DOCUMENTS

| | | |
|---|---|---|
| JP | 64-22849 | 1/1989 |
| JP | 6-179641 A | 6/1994 |
| WO | WO 96/07642 A1 | 3/1996 |

OTHER PUBLICATIONS

Gou, Da-Ming et al., "A Practical Chemoenzymatic Synthesis of the Taxol C-13 Side Chain N-Benzoyl-(2R,3S)-3-phenylisoserine", J. Org. Chem., vol. 58, No. 5, 1993, pp. 1287-1289.

Lee, Sang-Hyeup et al., "Efficient asymmetric synthesis of 2,3-diamino-3-phenylpropanoic acid derivatives", TETRAHEDRON, vol. 57, No. 11, Mar. 2001, pp. 2139-2145.

Lee, Sang-Hyeup et al., "Efficient Syntheses and Ring-Opening Reactions of trans- and cis-Oxazoline-5-carboxylates", Organic Letters, vol. 2, No. 9, May 2000, pp. 1243-1246.

* cited by examiner

PROCESS FOR PRODUCING 3-AMINO-2-HYDROXYPROPIONIC ACID DERIVATIVES

TECHNICAL FIELD

The present invention relates to a process for preparing 3-amino-2-hydroxypropionic acid derivatives represented by the following general formula (1):

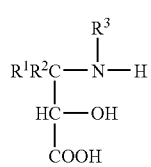

wherein $R^1$, $R^2$ and $R^3$, independently from each other, represent a hydrogen atom, a substituted or unsubstituted alkyl group having 1 to 30 carbon atoms, a substituted or unsubstituted aryl group having 6 to 30 carbon atoms, or a substituted or unsubstituted aralkyl group having 7 to 30 carbon atoms.

3-Amino-2-hydroxypropionic acid derivatives of the general formula (1) [hereinafter, also referred to as 3-amino-2-hydroxypropionic acid derivatives (1)] are useful compounds as an intermediate of a medicine. Among others, 3-amino-2-hydroxy-4-phenylbutyric acid [a compound of the general formula (1) wherein $R^1$ is a benzyl group, $R^2$ and $R^3$ are hydrogen atoms] is particularly important: (2S,3R)-isomer (i.e. threo-isomer) of the compound can be led, for example, to an immunostimulating anticancer agent, Bestatin [J. Antibiotics, vol. 29, p. 600 (1976)]; on the other hand, (2S,3S)-isomer (i.e. erythro-isomer) of the compound can be led, for example, to a HIV protease inhibitor, KNI-227 (JP-A-05/170722).

BACKGROUND ART

Several processes for preparing 3-amino-2-hydroxypropionic acid derivatives (1) are known in the art. One representative is a process comprising a stereoselective addition reaction of a cyanide compound onto an aminoaldehyde derived from an amino acid [J. Chem. Soc., Chem. Commun., p. 938 (1989); Synthesis, p. 703 (1989); EP-B-341462; JP-A-02/17165; JP-A-02/28144; JP-A-02/56547; JP-A-08/165,274; JP-A-10/231,280]. However, the above process must use a cyanogen compound having a very high toxicity, and therefore, is problematic as an industrial production process.

Other processes, for example, a process comprising decomposing an optically active 2-azetidinone derivative obtained through a [2+2] cyclo addition of a chiral imine and a ketene compound [Tetrahedron Lett., vol. 31, p. 3031 (1990)], and a process comprising a stereoselective alkylation and a stereoselective amination of a chiral glyoxylate [J. Org. Chem., vol. 54, p. 4235 (1989)] are also known in the art. However, all these processes are also problematic as an industrial production process because they need many steps and complicated procedures, for example.

Furthermore, a process comprising stereoselectively alkylating a malic acid ester, selectively converting one of carboxyl groups into an azide, and then passing through a rearrangement reaction of Curtius type [EP-B-379288; Tetrahedron Lett., vol. 33, p. 6803 (1992)], as well as, a process comprising selectively converting one of carboxyl groups into an amide in a similar manner and then passing through a rearrangement reaction of Hofmann type [Tetrahedron Lett., vol. 33, p. 6763 (1992)] are known in the art. However, these processes are also unsuitable for an industrial production because they use an expensive base (e.g. lithium hexamethyldisilazane and lithium amide), an explosive azide compound, a toxic lead compound, or the like.

On the other hand, as a process for preparing 3-amino-2-hydroxypropionic acid derivatives (1) which does not use specially dangerous reagents and is suitable for an industrial production, a process comprising a stereoselective hydrolysis of a dihaloketone derivative derived from an amino acid (JP-A-10/59909) is known in the art. In this process, for example, an erythro form [i.e. (2S,3S)-isomer or (2R,3R)-isomer, respectively] of 3-amino-2-hydroxypropionic acid derivative (1) is predominantly obtained from a (S)-amino acid or (R)-amino acid, but there is a limitation as a process for obtaining a threo form [i.e. (2R,3S)-isomer or (2S,3R)-isomer] of 3-amino-2-hydroxypropionic acid derivative (1) which is a diastereomer of the former compound.

In addition, a process is known in the art which comprises reacting the above erythro form [i.e. (2S,3S)-isomer or (2R,3R)-isomer, respectively] of 3-amino-2-hydroxypropionic acid derivative (1) with a carbonylation agent to obtain an erythro form of an oxazolidinone derivative, and then isomerizing it with a strong base to a threo form [i.e. (2R,3S)-isomer or (2S,3R)-isomer] of the oxazolidinone derivative which is a diastereomer of the former compound (JP-A-09/169,744). However, this process must use phosgene having a very high toxicity as a carbonylation agent, and an expensive base such as an alkali metal or alkaline earth metal alkoxide, an alkali metal amide or an alkyl lithium compound or an alkylmagnesium halide as a strong base. Accordingly, the process is unsuitable for an industrial production.

Accordingly, there is a strong need for establishment of a novel production process suitable for an industrial production of 3-amino-2-hydroxypropionic acid derivatives (1) by a methodology different from that of the prior art, in particular, for establishment of an industrial production process for desired stereoisomeric (e.g. threo) 3-amino-2-hydroxypropionic acid derivatives (1).

In view of the above circumstances, the object of the present invention was to provide a process for preparing 3-amino-2-hydroxypropionic acid derivatives (1) which does not use dangerous reagents, is economically advantageous, and is suitable for an industrial production.

DISCLOSURE OF THE INVENTION

The present inventors have intensively investigated in order to solve the above problems. As a result, they found that 3-amino-2-hydroxypropionic acid derivatives (1) can be prepared without using dangerous reagents, by converting a hydroxyl group of N-alkoxycarbonyl-3-amino-2-hydroxypropionic acid derivatives having a steric configuration at 2-position carbon reverse to that of desired stereoisomeric 3-amino-2-hydroxypropionic acid derivatives into a leaving group, and then inverting the steric configuration at 2-position carbon.

In addition, they found that impurities are apt to be produced secondarily and the yield and quality of 3-amino-2-hydroxypropionic acid derivatives (1) tend to reduce, if intermediate substituted-3-amino-2-hydroxypropionic acid derivatives having an inverted steric configuration at 2-position carbon are supplied to a next step without isolation and/or purification to a pure form. However, they also found that 3-amino-2-hydroxypropionic acid derivatives (1) can be stably produced in a high yield and a high quality, by contacting the intermediate substituted-3-amino-2-hydroxypropionic acid derivatives having an inverted steric configuration at 2-position carbon, without isolation and/or purification to a pure form, with water under acidic to neutral conditions and subjecting the mixture to heat treatment.

On the basis of the above findings, the present invention was accomplished as a process capable of preparing 3-amino-2-hydroxypropionic acid derivatives (1) in a safe and economically advantageous manner and in a form suitable for an industrial production.

Thus, the present invention relates to a process for preparing 3-amino-2-hydroxypropionic acid derivatives represented by the general formula (1):

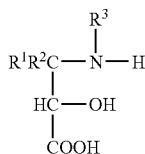
(1)

wherein $R^1$, $R^2$ and $R^3$, independently from each other, represent a hydrogen atom, a substituted or unsubstituted alkyl group having 1 to 30 carbon atoms, a substituted or unsubstituted aryl group having 6 to 30 carbon atoms, or a substituted or unsubstituted aralkyl group having 7 to 30 carbon atoms, which comprises the steps of:

converting N-protected-3-amino-2-hydroxypropionic acid derivatives [hereinafter, also referred to as N-protected-3-amino-2-hydroxypropionic acid derivatives (2)] having a steric configuration at 2-position carbon reverse to that of the above compounds (1) and represented by the general formula (2):

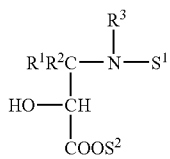
(2)

wherein $R^1$, $R^2$ and $R^3$ are as defined above;
$S^1$ represents an urethane-type protecting group for an amino group represented by —$COOR^4$, wherein $R^4$ represents a substituted or unsubstituted alkyl group having 1 to 30 carbon atoms, a substituted or unsubstituted aryl group having 6 to 30 carbon atoms, or a substituted or unsubstituted aralkyl group having 7 to 30 carbon atoms; and
$S^2$ represents a hydrogen atom or an ester residue; into N-protected-3-aminopropionic acid derivatives [hereinafter, also referred to as N-protected-3-aminopropionic acid derivatives (3)] represented by the general formula (3):

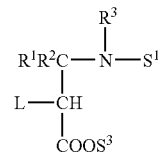
(3)

wherein $R^1$, $R^2$, $R^3$ and $S^1$ are as defined above;
L represents a leaving group; and
$S^3$ represents a hydrogen atom or an ester residue;
then converting the derivatives (3) into substituted-3-amino-2-hydroxypropionic acid derivatives [hereinafter, also referred to as substituted-3-amino-2-hydroxypropionic acid derivatives (4)] having an inverted steric configuration at 2-position carbon and represented by the general formula (4):

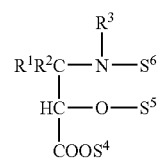
(4)

wherein $R^1$, $R^2$ and $R^3$ are as defined above;
$S^4$ represents a hydrogen atom or an ester residue;
$S^5$ represents a hydrogen atom or a substituent derived from $S^1$;
$S^6$ represents $S^1$ when $S^5$ is a hydrogen atom, or a substituent derived from $S^1$, taken together with $S^5$, when $S^5$ is a substituent derived from $S^1$; and
$S^1$ is as defined above;
and then converting the derivatives (4) into 3-amino-2-hydroxypropionic acid derivatives (1).

The present invention also relates to a process for preparing the 3-amino-2-hydroxypropionic acid derivatives in a high quality and a high yield, which comprises:

in the step of inverting the steric configuration at 2-position carbon of N-protected-3-aminopropionic acid derivatives (3) to convert the derivatives into substituted-3-amino-2-hydroxypropionic acid derivatives (4), contacting the resultant substituted-3-amino-2-hydroxypropionic acid derivatives (4), without isolation and/or purification, with water and subjecting the mixture to heat treatment.

BEST MODE FOR PRACTICING THE INVENTION

Hereinafter, the present invention is described in more detail.

Basically, the process according to the present invention consists of three steps as shown in the following scheme:
the first step wherein leaving group L is introduced into N-protected-3-amino-2-hydroxypropionic acid derivatives (2) to convert the derivatives into N-protected-3-aminopropionic acid derivatives (3);
the second step wherein a steric configuration at 2-position carbon of N-protected-3-aminopropionic acid derivatives (3) is inverted to convert the derivatives into substituted-3-amino-2-hydroxypropionic acid derivatives (4); and the third step wherein substituted-3-amino-2-hydroxypropionic acid derivatives (4) are converted into 3-amino-2-hydroxypropionic acid derivatives (1).

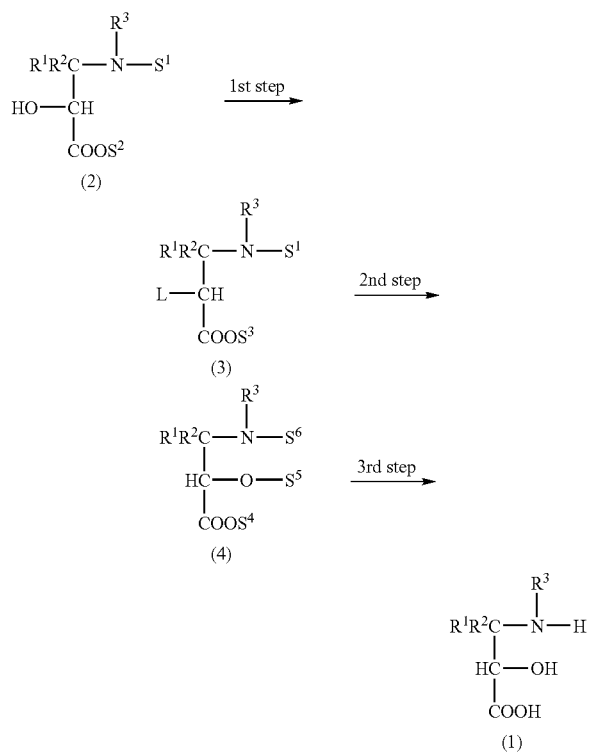

Firstly described is the first step wherein leaving group L is introduced into N-protected-3-amino-2-hydroxypropionic acid derivatives (2) to convert the derivatives into N-protected-3-aminopropionic acid derivatives (3).

In the N-protected-3-amino-2-hydroxypropionic acid derivatives (2) and the N-protected-3-aminopropionic acid derivatives (3), $R^1$, $R^2$ and $R^3$, independently from each other, represent a hydrogen atom, a substituted or unsubstituted alkyl group having 1 to 30 carbon atoms, a substituted or unsubstituted aryl group having 6 to 30 carbon atoms, or a substituted or unsubstituted aralkyl group having 7 to 30 carbon atoms.

The above alkyl group is not limited to a particular one and includes, for example, a methyl group, an ethyl group, a propyl group, an isopropyl group, an isobutyl group, a cyclohexylmethyl group or the like. The above aryl group is not limited to a particular one and includes, for example, a phenyl group, a p-chlorophenyl group, a p-fluorophenyl group, a p-methoxyphenyl group, a 1-naphthyl group, a 2-naphthyl group or the like. The above aralkyl group is not limited to a particular one and includes, for example, a benzyl group, a p-methoxybenzyl group, a 3-phenylpropyl group, a 2-phenylpropyl group or the like.

As to the combination of $R^1$ and $R^2$, a combination wherein one of these is a hydrogen atom and the other is a substituted or unsubstituted alkyl group having 1 to 30 carbon atoms, a substituted or unsubstituted aryl group having 6 to 30 carbon atoms, or a substituted or unsubstituted aralkyl group having 7 to 30 carbon atoms is preferable. Among others, a combination wherein one of these is a hydrogen atom and the other is a substituted or unsubstituted aralkyl group having 7 to 30 carbon atoms is preferable. In particular, a combination wherein one of these is a hydrogen atom and the other is a substituted or unsubstituted benzyl group is preferable, and especially, a combination wherein one of these is a hydrogen atom and the other is an unsubstituted benzyl group is preferable.

Also, $R^3$ is preferably a hydrogen atom, a substituted or unsubstituted alkyl group having 1 to 30 carbon atoms, or a substituted or unsubstituted aralkyl group having 7 to 30 carbon atoms. In particular, $R^3$ is preferably a hydrogen atom, a lower alkyl group having 1 to 4 carbon atoms, or a substituted or unsubstituted benzyl group, and especially preferable $R^3$ is a hydrogen atom, a methyl group, an ethyl group, or a benzyl group. Most preferable $R^3$ is a hydrogen atom.

In the N-protected-3-amino-2-hydroxypropionic acid derivatives (2) and the N-protected-3-aminopropionic acid derivatives (3), $S^1$ is an urethane-type protecting group for an amino group. The above urethane-type protecting group for an amino group is not limited to a particular one and may be selected from the protecting groups as described, for example, in PROTECTIVE GROUPS IN ORGANIC SYNTHESIS, 2nd ed., JOHN WILLY & SONS publ. (1991). In general, from the viewpoint of an easy handling, an inexpensiveness, a convenient synthesis of substrate compounds and the like, a lower alkoxycarbonyl group having 1 to 4 carbn atoms or a substituted or unsubstituted aralkyloxycarbonyl group having 7 to 10 carbon atoms is preferably used, for example. Among others, a methoxycarbonyl group, an ethoxycarbonyl group, a t-butoxycarbonyl group, a benzyloxycarbonyl group or the like is preferably used, and especially, a methoxycarbonyl group or an ethoxycarbonyl group is preferably used. An ethoxycarbonyl group is most preferably used.

Also, $S^2$ in the N-protected-3-amino-2-hydroxypropionic acid derivatives (2) and $S^3$ in the N-protected-3-aminopropionic acid derivatives (3) represent a hydrogen atom or an ester residue. The above ester residue represents a monovalent organic group which can serve as an ester-type protecting group for a carboxyl group, for example, by being included in a structure represented by —$COOS^2$ (—$COOS^3$). The above monovalent organic group is not limited to a particular one if it has an effect of protecting the carboxyl group, and may be selected from the ester-type protecting groups as described, for example, in PROTECTIVE GROUPS IN ORGANIC SYNTHESIS, 2nd ed., JOHN WILLY & SONS publ. (1991). Among others, a lower alkyl group having 1 to 4 carbon atoms or a substituted or unsubstituted benzyl group is preferably used. A lower alkyl group having 1 to 4 carbon atoms is more preferably used and a methyl group or an ethyl group is further preferably used. A methyl group is most preferably used.

In the N-protected-3-aminopropionic acid derivatives (3), L represents a leaving group. The above L is not limited to a particular one and preferably includes, for example, a sulfonyloxy group, a halosulfinyloxy group or a halogen atom. The above sulfonyloxy group is not limited to a particular one and preferably includes, for example, a substituted or unsubstituted lower alkylsulfonyloxy group, in particular a lower alkylsulfonyloxy group having 1 to 4 carbon atoms, or a substituted or unsubstituted arylsulfonyloxy group, in particular arylsulfonyloxy group having 6 to 10 carbon atoms. The above lower alkylsulfonyloxy group includes, for example, a methanesulfonyloxy group, an ethanesulfonyloxy group or the like, and the above arylsulfonyloxy group includes a p-toluenesulfonyloxy group, an o-, p- or m-nitrobenzenesulfonyloxy group or the like.

Among others, a methanesulfonyloxy group is preferably used. The above halosulfinyloxy group includes, for example, a chlorosulfinyloxy group, a bromosulfinyloxy group or the like, and a chlorosulfinyloxy group is particularly preferable. The above halogen atom includes, for example, a chlorine atom, a bromine atom, an iodine atom or the like, and a chlorine atom is particularly preferable.

In the introduction of the above leaving group L into the 3-amino-2-hydroxypropionic acid derivatives (2), any of known leaving group-introducing agents may be used without any limitation.

If the leaving group L is a sulfonyloxy group, a corresponding sulfonyl halide compound is preferably reacted as a leaving group-introducing agent. In general, cheap and easily available sulfonyl chloride compounds are preferably used as the above sulfonyl halide compound. Among others, methanesulfonyl chloride, ethanesulfonyl chloride, benzenesulfonyl chloride, p-toluenesulfonyl chloride, nitrobenzenesulfonyl chloride or the like is preferably used, and especially, methanesulfonyl chloride is preferably used. The amount of the above sulfonyl halide compounds used is not limited to a particular range, and they are usually used in a molar amount of 1 to 10-fold, preferably in a molar amount of 1 to 5-fold, and more preferably in a molar amount of 1 to 2-fold, relative to the 3-amino-2-hydroxypropionic acid derivatives (2).

Also, in order to progress the above reaction with sulfonyl halide compounds smoothly, the reaction may be carried out in the coexistence of a base. The base is not limited to a particular one and amines, particularly tertiary amines may be preferably used. The above amines are not limited to a particular one and include triethylamine, diisopropylethylamine, pyridine or the like. From the viewpoint of practical use, cheap bases are preferable and generally triethylamine is preferably used. The amount of the above amines used is not limited to a prticular range, and they are usually used in a molar amount of 1 to 20-fold, preferably in a molar amount of 1 to 5-fold, and more preferably in a molar amount of 1 to 3-fold, relative to the 3-amino-2-hydroxypropionic acid derivatives (2). The reaction temperature can not be defined uniformly and is usually from −20° to 80° C., preferably from −10° to 50° C.

In the introduction of the above L into the 3-amino-2-hydroxypropionic acid derivatives (2), if L is a halosulfinyloxy group or a halogen atom, thionyl halides are preferably used for the reaction as a leaving group-introducing agent. Usually, cheap and easily available thionyl chloride is preferably used as the above thionyl halides. The amount of the above thionyl halides used is not limited to a particular range, and they are usually used in a molar amount of 1 to 10-fold, preferably in a molar amount of 1 to 5-fold, and more preferably in a molar amount of 2 to 3-fold, relative to the 3-amino-2-hydroxypropionic acid derivatives (2). The reaction temperature can not be defined uniformly and is usually from −20° to 120° C., preferably from 0° to 80° C.

Reaction solvents used for the introduction of the above leaving group L are not limited to a particular one, if they are essentially inert to the above sulfonyl halide compounds or the above thionyl halides. Examples of the reaction solvents include, for example, aliphatic hydrocarbons such as hexane, heptane or methylcyclohexane; aromatic hydrocarbons such as toluene or xylene; halogenated hydrocarbons such as methylene chloride or chloroform; ethers such as tetrahydrofuran, 1,4-dioxane or t-butyl methyl ether; aliphatic acid esters such as methyl acetate, ethyl acetate or isopropyl acetate; aprotic polar solvents such as acetonitrile, N,N-dimethyl formamide or dimethyl sulfoxide. Among others, the above aromatic hydrocarbons, the above ethers, or the above aliphatic acid esters are preferably used. Toluene is a particularly preferable aromatic hydrocarbon, tetrahydrofuran is a particularly preferable ether, and ethyl acetate is a particularly preferable aliphatic acid ester. These solvents may be used alone or in a mixture of two or more solvents. Besides, if the reaction mixture of the 3-amino-2-hydroxypropionic acid derivatives (2) and the above sulfonyl halide compounds or the above thionyl halides is fluid, for example, in a solution state, the above reaction solvents are not necessarily needed.

The above $S^2$ and $S^3$ may be the same. Also, it is simple and convenient if they are the same, and generally, they are often the same. However, they may be converted by esterification, hydrolysis, transesterification or the like under the conditions of this reaction. Furthermore, if necessary, known esterification, hydrolysis, transesterification or the like may be introduced into this step, and they may be freely selected in a range of not affecting the step. For example, if $S^2$ is a hydrogen atom in the N-protected-3-amino-2-hydroxypropionic acid derivatives (2), and if thionyl halides are reacted with the derivatives to introduce a halogen atom as leaving group L, then alcohol treatment may be preferably carried out to derive an ester form of N-protected-3-aminopropionic acid derivatives (3) ($S^3$ is an ester residue) by the action of hydrogen halides and/or thionyl halides present in excess.

In this step, the selection of a leaving group-introducing agent used for the introduction of the above leaving group L or the combination of $S^2$ and the leaving group L is not limited to a particular one. In general, if $S^2$ in the N-protected-3-amino-2-hydroxypropionic acid derivatives (2) is a hydrogen atom, thionyl halides (i.e. leaving group L is a chlorosulfinyloxy group or a halogen atom) are preferably used. Also, if $S^2$ is an ester residue, sulfonyl halide compounds (i.e. leaving group L is a sulfonyloxy group) or thionyl halides (i.e. leaving group L is a chlorosulfinyloxy group or a halogen atom) are preferably used, and especially, sulfonyl halide compounds (i.e. leaving group L is a sulfonyloxy group) are preferably used. Most preferable combination of $S^2$ and leaving group L is that wherein $S^2$ is an ester residue and leaving group L is a sulfonyloxy group.

The N-protected-3-aminopropionic acid derivatives (3) synthesized as described above may be isolated and/or purified by a conventional method such as extraction, crystallization, distillation, chromatography or the like. However, from the operational and/or economical viewpoint in the industrial production, the products may be used in the next reaction as they are without isolation and/or purification by the above conventional method.

Next described is the second step wherein a steric configuration at 2-position carbon of N-protected-3-aminopropionic acid derivatives (3) is inverted to convert the derivatives into substituted-3-amino-2-hydroxypropionic acid derivatives (4).

In this step, the N-protected-3-aminopropionic acid derivatives (3) obtained in the first step can be converted into substituted-3-amino-2-hydroxypropionic acid derivatives (4) having an inverted steric configuration at 2-position carbon, in a high steric inversion ratio. In this case, the N-protected-3-aminopropionic acid derivatives (3) synthesized in the above first step may be occasionally converted into substituted-3-amino-2-hydroxypropionic acid derivatives (4) having an inverted steric configuration at 2-position carbon under reaction conditions of the above first step. However, the process is included within the production process according to the present invention so far as the above N-protected-3-aminopropionic acid derivatives (3) are once formed as an intermediate.

In this step, the inversion of a steric configuration at 2-position carbon can proceed with an essentially perfect inversion. The steric inversion ratio at 2-position carbon in the products can be expected to be at least 95% or more, usually 98% or more, preferably 100%. In this connection, the steric inversion ratio means, as a general concept, a ratio of enantiomer excess (% e.e.) or diastereomer excess (% d.e.) of a product having an inverted steric configuration at 2-position carbon [in this case, substituted-3-amino-2-hydroxypropionic acid derivatives (4)] to enantiomer excess (% e.e.) or diastereomer excess (% d.e.) of a starting material [in this case, N-protected-3-aminopropionic acid derivatives (3)].

In this step, oxazolidinone derivatives are usually obtained as the substituted-3-amino-2-hydroxypropionic acid derivatives (4) having an inverted steric configuration at 2-position carbon. However, as described below in more detail, for example, if water coexists at the beginning of this step for the purpose of producing 3-amino-2-hydroxypropionic acid derivatives in a high quality and a high yield, plural compounds can be formed as the substituted-3-amino-2-hydroxypropionic acid derivatives (4) having an inverted steric configuration at 2-position carbon. The typical examples are shown in the following scheme:

N-alkoxycarbonyl-3-amino-2-hydroxypropionic acid derivative (4b) can be formed by hydrolysis of the above oxazolinium derivative (4a), or by direct substitution of leaving group L of N-protected-3-aminopropionic acid derivative (3) with water.

The oxazolidinone derivative (4c) can be formed by hydrolysis or the like of the above oxazolinium derivative (4a), or by substitution of an alkoxy group (—OR$^4$) of an alkoxycarbonyl group (—COOR$^4$) of the above N-alkoxycarbonyl-3-amino-2-hydroxypropionic acid derivative (4b) with a 2-position hydroxyl group in the same molecule. In this connection, the oxazolidinone derivative (4c) can be formed whether water coexists in this step or not.

In the substituted-3-amino-2-hydroxypropionic acid derivatives (4) obtained in this step, S$^4$ (or S$^7$, S$^8$ or S$^9$) represents a hydrogen atom or an ester residue. The above ester residue represents a monovalent organic group which can serve as an ester-type protecting group for a carboxyl group, for example, by being included in a structure represented by —COOS$^4$ or the like. The above monovalent organic group is not limited to a particular one if it has an effect of protecting the carboxyl group, and may be selecter from the ester-type protecting groups as described, for example, in PROTECTIVE GROUPS IN ORGANIC SYNTHESIS, 2nd ed., JOHN WILLY & SONS publ. (1991).

Among others, a lower alkyl group having 1 to 4 carbon

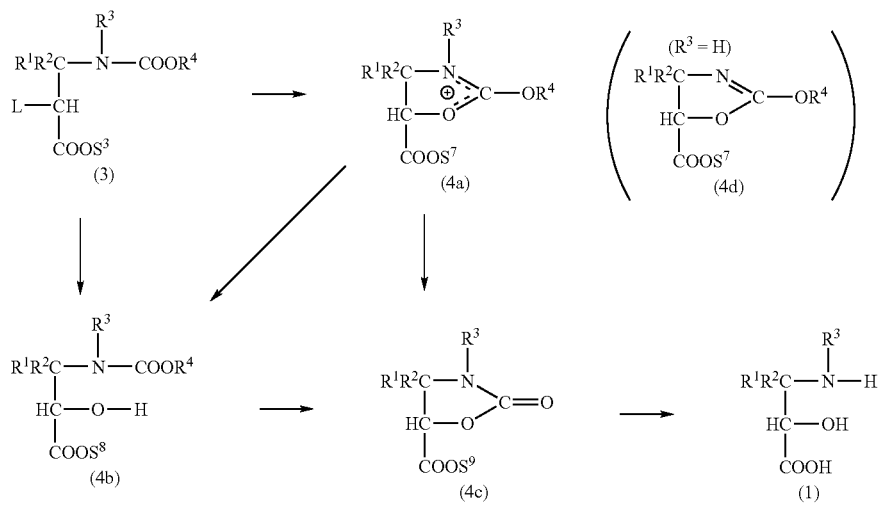

wherein R$^1$, R$^2$, R$^3$, R$^4$ and S$^3$ are as defined above;

L represents a leaving group; and

S$^7$, S$^8$ and S$^9$ represent a hydrogen atom or an ester residue.

The formation mechanism of these inversion products is presumed as follows.

Firstly, oxazolinium derivative (4a) is formed by substitution of leaving group L of N-protected-3-aminopropionic acid derivative (3) through a nucleophilic substitution reaction by carbonyl oxygen of an alkoxycarbonyl group (—COOR$^4$) in the same molecule. The leaving group L eliminated in this substitution reaction can form a salt with oxazolinium derivative (4a) as a counter anion. If R$^3$ is a hydrogen atom, of course, the structure of the oxazolinium derivative (4a) may be represented as oxazoline derivative (4d) formed by deprotonation.

atoms or a substituted or unsubstituted benzyl group is preferably used. A lower alkyl group having 1 to 4 carbon atoms is more preferably used and a methyl group or an ethyl group is further preferably used. A methyl group is most preferably used.

S$^3$ in the N-protected-3-aminopropionic acid derivatives (3) and S$^4$ (or S$^7$, S$^8$ or S$^9$) in the substituted-3-amino-2-hydroxypropionic acid derivatives (4) may be the same. It is simple and convenient if they are the same, and generally, they are often the same. However, they may be converted by esterification, hydrolysis, transesterification or the like under the conditions of this reaction. Furthermore, if necessary, known esterification, hydrolysis, transesterification or the like may be introduced into this step, and they may be freely selected in a range of not affecting the step. For example, if S$^3$ is an ester residue in the 3-aminopropionic acid derivatives (3), for example, this reaction may be preferably carried out in the presence of water (or using water as a reaction solvent), and if necessary, the ester site may be hydrolyzed, to derive substituted-3-amino-2-hydroxypropionic acid derivatives (4) wherein $S^4$ is a hydrogen atom.

Next, reaction conditions of the second step are described.

Preferably, this reaction is carried out under heating. The reaction temperature is not limited to a particular range if it is below the boiling point of the reaction mixture. It may be preferably above 40° C., more preferably above 60° C., and most preferably above 80° C. In general, as the temperature becomes higher, the reaction proceeds more rapidly.

Also, in this step, an acid treatment or a base treatment may be carried out for the purpose of promoting the reaction, if necessary, by coexistence or addition of a suitable amount of an acidic substance or a basic substance as a reaction accelerator. This treatment allows the reaction to proceed repidly at a lower temperature, and therefore, it is possible to carry out the inversion step at a milder treating temperature or a far milder treating temperature. The treating temperature in this case is usually below about 40° C., and it is also possible to carry out the step at a temperature below about 20° C. It is particularly preferable to carry out the step in the coexistence of an acidic substance, because it has a high effect of promoting the reaction and it allows a later water treatment step to be carried out easily under an acidic to neutral condition.

The acidic substance is not limited to a particular one. Organic acids include, for example, sulfonic acids such as methanesulfonic acid, ethanesulfonic acid, p-toluenesulfonic acid, o-, p- or m-nitrobenzenesulfonic acid; carboxylic acids such as formic acid, acetic acid, trifluoroacetic acid or benzoic acid. Inorganic acids include, for example, hydrochloric acid, sulfuric acid, sulfurous acid, phosphoric acid or the like. Also, in this reaction, leaving group L is eliminated to produce secondarily a conjugate acid of the leaving group L represented by the following general formula (7):

$$L\text{-}H \qquad (7)$$

wherein L is as defined above, and the conjugate acid (7) of the leaving group L is also used as an acidic substance preferably.

The amount of acidic substances used is not limited to a particular range, and they are usually used in a molar amount of 0.01 to 100-fold, preferably in a molar amount of 0.05 to 50-fold, and more preferably in a molar amount of 0.1 to 20-fold, for example, relative to the N-protected-3-aminopropionic acid derivatives (3).

Also, the basic substance is not limited to a particular one, and weakly basic substances are preferably used. The weakly basic substances are not limited to particular ones. In general, basic substances showing a pKa value below 10, for example, of the conjugate acid in an aqueous solution are preferably used, and especially, those showing a pKa value below 5 are more preferably used. Specific examples include, for example, amines such as triethylamine, diisopropylamine or pyridine; carbonates such as sodium carbonate or potassium carbonate; hydrogen carbonates such as sodium hydrogencarbonate or potassium hydrogencarbonate. Organic solvents showing a weak basicity such as N,N-dimethyl formamide, dimethyl sulfoxide or the like are also within a range of selection.

The amount of the basic substances used is not limited to a particular range, and they are usually used in a molar amount of 0.01 to 100-fold, preferably in a molar amount of 0.05 to 50-fold, and more preferably in a molar amount of 0.1 to 20-fold, for example, relative to the N-protected-3-aminopropionic acid derivatives (3).

In general, acidic substances are preferably used as the above reaction accelerator, bacause they are easily removed from the reaction mixture after completion of the reaction and they have small influence in the yield and quality of the products even if they are brought in the next step as they are.

Reaction solvents used in this reaction are not limited to particular ones, and various solvents usually used may be used. Examples of the reaction solvents include, for example, aliphatic hydrocarbons such as hexane, heptane or methylcyclohexane; aromatic hydrocarbons such as toluene or xylene; halogenated hydrocarbons such as methylene chloride or chloroform; ethers such as tetrahydrofuran, 1,4-dioxane or t-butyl methyl ether; aliphatic acid esters such as methyl acetate, ethyl acetate or isopropyl acetate; nitriles such as acetonitrile; alcohols such as methanol, ethanol, isopropanol or benzyl alcohol; water. Among others, aromatic hydrocarbons, ethers, aliphatic acid esters or water are preferably used. Toluene is a particularly preferable aromatic hydrocarbon, 1,4-dioxane is a particularly preferable ether, and ethyl acetate is a particularly preferable aliphatic acid ester. These solvents may be used alone or in a mixture of two or more solvents. Besides, if the above reaction accelerator is liquid at the above reaction temperature, the above reaction accelerator may be used so as to also serve as a reaction solvent.

The substituted-3-amino-2-hydroxypropionic acid derivatives (4) synthesized as described above may be isolated and/or purified by a conventional mathod such as extraction, crystallization, distillation, chromatography or the like. Alternatively, the reaction mixture may be used next in the third step as it is.

In the meantime, if the above reaction mixture, in particular, the reaction mixture obtained by carrying out the above second step under non-aqueous conditions is next supplied to the third step as it is without isolation and/or purification, an impurity is apt to be produced secondarily and the yield tends to decrease. The present inventors have intensively investigated the causes of the secondary production of the impurity as well as the decrease of the yield. As a result, they found that a by-product [hereinafter, also referred to as by-product (8)] represented by the following general formula (8):

$$L\text{-}R^4 \qquad (8)$$

wherein L and $R^4$ are as defined above, is produced secondarily in the second step, and it serves as a certain alkylating agent, whereby a N-substituted-3-amino-2-hydroxypropionic acid derivative [hereinafter, also referred to as impurity (9)], in which $R^4$ is introduced onto the nitrogen atom in the above 3-amino-2-hydroxypropionic acid derivatives (1), and which is represented by the following general formula (9):

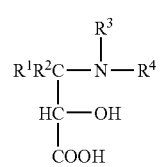

(9)

wherein $R^1$, $R^2$, $R^3$ and $R^4$ are as defined above, is produced secondarily as an impurity and the derivative causes the decrease of the yield and quality of the 3-amino-2-hydroxypropionic acid derivatives (1).

Accordingly, in order to minimize the secondary production of the impurity (9) and to maximize the yield in the third step, it is preferable to remove the above by-product (8) responsible for the above impurity (9), for example, by carrying out isolation and/or purification of the above substituted-3-amino-2-hydroxypropionic acid derivatives (4) to a pure form, for example, by obtaining the derivatives as crystals by crystallization.

If the above substituted-3-amino-2-hydroxypropionic acid derivatives (4) obtained according to the present invention, in particular, 2-oxazolidinone-5-carboxylic acid ester derivatives (4') [compounds of the general formula (4) wherein $S^4$ is an ester residue and $S^5$ and $S^6$, taken together, are a carbonyl group] are isolated and/or purified by crystallization into an almost pure form (as crystals), the derivatives may be purified and crystallized well using aromatic hydrocarbons as a solvent for crystallization. The aromatic hydrocarbons are not limited to particular ones, and include benzene, toluene, o-, m- or p-xylene, mesitylene, chlorobenzene or the like. Among others, toluene is used preferably.

In the crystallization of the above substituted-3-amino-2-hydroxypropionic acid derivatives (4), usual crystallization procedures such as cooling and/or concentration may be used without any limitation.

In the above crystallization, a solvent in a solution of the above substituted-3-amino-2-hydroxypropionic acid derivatives (4) other than the above aromatic hydrocarbons may be replaced to a solvent selected from the above aromatic hydrocarbons. Of course, with the progress of the solvent-replacement procedures, the above substituted-3-amino-2-hydroxypropionic acid derivatives (4) may be crystallized (so-called solvent-replacement crystallization). The above solvents other than aromatic hydrocarbons are not limited to particular ones, and include, for example, acetic acid esters such as ethyl acetate or isopropyl acetate; ethers such as tert-butyl methyl ether, tetrahydrofuran or 1,4-dioxane; alcohols such as methanol, ethanol or isopropanol; water.

The concentration of crystallization solution may be in a range capable of maintaining the fluidity of a crystallization solution. In general, the concentration is preferably below about 60% (w/v), more preferably below about 40% (w/v), and most preferably below about 20% (w/v).

The temperature at which the above crystallization is carried out is not limited to a particular range. In order to obtain a crystallization solution (slurry) having a good property, a slow progress of crystallization, for example, by a slow cooling is suitable. Also, addition of seed crystals is suitable for smooth crystallization The above substituted-3-amino-2-hydroxypropionic acid derivatives (4) crystallized may be separated using usual solid-liquid separation procedures such as filtration, centrifugation or the like. If necessary, separated wet solids of the substituted-3-amino-2-hydroxypropionic acid derivatives (4) may be further washed using, for example, the above aromatic hydrocarbons, and then dried at atmospheric pressure or under reduced pressure.

On the other hand, if a reaction mixture containing the above substituted-3-amino-2-hydroxypropionic acid derivatives (4) is used as it is without isolation and/or purification, the above reaction mixture is contacted with water and subjected to heat treatment to hydrolyze the above by-products (8) responsible for the above impurity (9), whereby the above by-products (8) may be made harmless to obtain effects similar to those obtained when carrying out isolation and/or purification. The above heat treatment in contact with water may be carried out in the second step, after carrying out the conversion into the above substituted-3-amino-2-hydroxypropionic acid derivatives (4) in a non-aqueous system, or simultaneously with the inversion of a steric configuration at 2-position carbon of N-protected-3-aminopropionic acid derivatives (3) to convert into the above substituted-3-amino-2-hydroxypropionic acid derivatives (4) in the coexistence of water from the beginning.

Water is required to make the above by-products (8) responsible for the above impurity (9) harmless. The amount of water used is not limited to a particular range, and it is usually used in a molar amount above 1-fold, preferably in a molar amount above 10-fold, more preferably in a molar amount above 20-fold, and most preferably in a molar amount above 50-fold, relative to the N-protected-3-aminopropionic acid derivatives (3). In general, as the amount of water used becomes larger, the effects become larger and duration required for treatment may be shortened. In this connection, from the viewpoint of productivity, water is usually used in a molar amount below 1000-fold, preferably in a molar amount below 500-fold, and more preferably in a molar amount below 100-fold, although there is no problem even if a large amount of water is used.

The temperature of the above heat treatment carried out in contact with water is not limited to a particular range if the temperature is below the boiling point of the reaction mixture. In general, as the temperature becomes higher, the effects by the contact with water become larger and duration required for treatment may be shortened. The treating temperature varies depending on various conditions such as the kind of substituted-3-amino-2-hydroxypropionic acid derivatives (4), the amount of water used, the contact duration with water, the acidity of a reaction mixture or the like, and can not be defined uniformly. The temperature may be preferably above 40° C., more preferably above 60° C., and most preferably above 80° C.

The above contact with water is carried out under acidic to neutral conditions. In general, as the acidity becomes higher, the effects by the contact with water become larger and duration required for treatment may be shortened. The above contact is usually carried out under acidic to neutral conditions, preferably under acidic conditions, and more preferably under strongly acidic conditions. Also, a gradual shift from neutral to acidic conditions may be preferably carried out with the progress of the reaction.

In the above contact with water, in order to maintain the reaction under acidic to neutral conditions, preferably under acidic conditions, and more preferably strongly acidic conditions and/or in order to shift the reaction to these conditions, if necessary, the reaction may be preferably carried out in the coexistence of an acidic substance. The acidic substance is not limited to a particular one. For example, organic acids include sulfonic acids such as methanesulfonic acid, ethanesulfonic acid, p-toluenesulfonic acid, o-, p- or m-nitrobenzenesulfonic acid; carboxylic acids such as formic acid, acetic acid, trifluoroacetic acid or benzoic acid, and inorganic acids include hydrochloric acid, sulfuric acid, sulfurous acid, phosphoric acid or the like.

The amount of acidic substances used is not limited to a particular range, and they are usually used in a molar amount of 0.01 to 100-fold, preferably in a molar amount of 0.05 to 50-fold, and more preferably in a molar amount of 0.1 to 20-fold, for example, relative to N-protected-3-aminopropionic acid derivatives (3).

In this connection, if the acidity in the above contact with water is expressed using a pH value as an indicator (standard), the acidic to neutral conditions refer to usually a range below pH 9, preferably a range below pH 8, and more preferably a range below pH 7. Also, the acidic conditions refer to a range below pH 4 and the strongly acidic conditions refer to a range below pH 2.

Next described is the third step wherein substituted-3-amino-2-hydroxypropionic acid derivatives (4) are converted into 3-amino-2-hydroxypropionic acid derivatives (1).

In this step, the substituents to be eliminated (substituent $S^4$ on the oxygen atom of the carboxyl group, substituent $S^5$ on the oxygen atom at 2-position carbon, and substituent $S^6$ on the nitrogen atom at 3-position carbon) on the substituted-3-amino-2-hydroxypropionic acid derivatives (4) having an inverted steric configuration at 2-position carbon, which are obtained in the second step, are eliminated to convert into 3-amino-2-hydroxypropionic acid derivatives (1). If each of $S^4$, $S^5$ and $S^6$ is a hydrogen atom, substituents to be eliminated are not present on each of oxygen and nitrogen atoms, of course.

Methods for eliminating substituents to be eliminated are not limited to particular ones and include, for example, methods described in PROTECTIVE GROUPS IN ORGANIC SYNTHESIS, 2nd ed., JOHN WILLY & SONS publ. (1991). Although preferable methods vary depending on the kind of protecting groups, they include, for example, acid treatment, base treatment, hydrolysis, catalytic reduction, electrolytic reduction, Zn/AcOH treatment or the like. Among others, acid treatment or hydrolysis is convenient and generally used. In particular, hydrolysis is convenient and generally used. Hereinafter, a method by hydrolysis for eliminating the above substituents to be eliminated is specifically described.

In this step, the amount of water used for hydrolysis is not limited to a particular range, and it is usually used in a molar amount above 1-fold, preferably in a molar amount above 10-fold, more preferably in a molar amount above 20-fold, and most preferably in a molar amount above 50-fold, relative to substituted-3-amino-2-hydroxypropionic acid derivatives (4). Water may be used in an excess amount, also as a reaction solvent, and usually used so. In this connection, from the viewpoint of productivity, water is usually used in a molar amount below 1000-fold, preferably in a molar amount below 500-fold, and more preferably in a molar amount below 100-fold, although there is no problem even if a large amount of water is used. If the treatment of contact with water is carried out in the above second step, water used in the treatment of contact with water may be used for hydrolysis in this step as it is, of course.

In the above hydrolysis, various organic solvents usually used may coexist in a range not affecting the reaction, in addition to water used as reaction reagents. In general, the above substituted-3-amino-2-hydroxypropionic acid derivatives (4) have a tendency to dissolve hardly in water, and therefore, organic solvents having a high dissolubility may be used together for the purpose of promotion of the reaction, improvement of the property of the reaction solution or the like. Examples of the various organic solvents include aliphatic hydrocarbons such as hexane, heptane or methylcyclohexane; aromatic hydrocarbons such as toluene or xylene; halogenated hydrocarbons such as methylene chloride or chloroform; ethers such as tetrahydrofuran, 1,4-dioxane or t-butyl methyl ether; aliphatic acid esters such as methyl acetate, ethyl acetate or isopropyl acetate; ketones such as acetone, methyl ethyl ketone or cyclohexanone; aprotic polar solvents such as acetonitrile, N,N-dimethyl formamide or dimethyl sulfoxide; alcohols such as methanol, ethanol, isopropanol or benzyl alcohol. Among others, aromatic hydrocarbons or ethers are preferably used. Toluene is a particularly preferable aromatic hydrocarbon and 1,4-dioxane is a particularly preferable ether. These solvents may be used alone or in a mixture of two or more solvents. Of course, the use of these organic solvents includes the case wherein an organic solvent used in the previous step is used as it is without any solvent-replacement.

The above hydrolysis may be carried out under basic or acidic conditions using a base or an acid. In particular, if oxazolinium derivatives (4a) and oxazolidinone derivatives (4c) are hydrolysed, the hydrolysis is preferably carried out under basic conditions.

The base is not limited to a particular one. Although the basic substance (weak base) used in the second step may be used as it is, it is preferable to add a base (preferably strong base) separately. The base separately added is not limited to a particular one and includes, for example, alkali metal hydroxides such as lithium hydroxide, sodium hydroxide or potassium hydroxide; alkaline earth metal hydroxides such as magnesium hydroxide or calcium hydroxide. Among others, alkali metal hydroxides are preferably used, and especially, sodium hydroxide is preferably used. The amount of the bases used is not limited to a particular range, and they are usually used in a molar amount of 1 to 100-fold, preferably in a molar amount of 2 to 50-fold, and more preferably in a molar amount of 5 to 20-fold, relative to substituted-3-amino-2-hydroxypropionic acid derivatives (4). If a pH value of a reaction solution is used as an indicator (standard), the value is usually above pH 10, preferably above pH 12, and more preferably above pH 14.

On the other hand, in the case of N-alkoxycarbonyl-3-amino-2-hydroxypropionic acid derivatives (4b), hydrolysis may be suitably carried out under acidic conditions as well. The acid is not limited to a particular one. Although the conjugate acid (7) of leaving group L produced secondarily in the second step and also the acidic substance used in the second step may be used as they are, an acid (preferably strong acid) may be added further. The acid separately added is not limited to a particular one. Organic acids include, for example, sulfonic acids such as methanesulfonic acid, ethanesulfonic acid, p-toluenesulfonic acid, o-, p- or m-nitrobenzenesulfonic acid; carboxylic acids such as formic acid, acetic acid, trifluoroacetic acid or benzoic acid, and inorganic acids include hydrochloric acid, sulfuric acid, sulfurous acid, phosphoric acid or the like. The amount of the acids used is not limited to a particular range, and they are usually used in a molar amount of 1 to 100-fold, preferably in a molar amount of 2 to 50-fold, more preferably in a molar amount of 5 to 20-fold, relative to substituted-3-amino-2-hydroxypropionic acid derivatives (4).

The reaction temperature of the above hydrolysis is not limited to a particular range if it is below the boiling point of the reaction mixture. The reaction temperature may be preferably above 40° C., more preferably above 60° C., and most preferably above 80° C. In general, as the temperature becomes higher, the reaction proceeds more rapidly.

The 3-amino-2-hydroxypropionic acid derivatives (1) synthesized as described above may be isolated by a conventional method such as extraction, crystallization, distillation, chromatography or the like. However, the derivatives are preferably isolated by a convenient and efficient crystallization process as described below.

The crystallization process comprises converting an acid or a base coexisting in an acidic or basic aqueous solution of 3-amino-2-hydroxypropionic acid derivatives (1), in particular, an aqueous solution obtained in the above third step

[step of converting substituted-3-amino-2-hydroxypropionic acid derivatives (4) into 3-amino-2-hydroxypropionic acid derivatives (1)], into a salt soluble in an organic solvent and/or water by neutralization, whereby precipitating 3-amino-2-hydroxypropionic acid derivatives (1) from a medium consisting of water or a mixture of an organic solvent and water, and at the same time, dissolving the salt formed in said medium.

The salt soluble in an organic solvent and/or water is not limited to a particular one and includes, for example, alkali metal salts such as lithium salts, sodium salts or potassium salts; alkaline earth metal salts such as magnesium salts or calcium salts; ammonium salts. Among others, alkali metal salts are preferable and lithium salts and sodium salts are more preferable.

The alkali metal salts are not limited to particular ones. Alkali metal halides such as lithium halides or sodium halides are preferable, alkali metal chlorides and alkali metal bromides are more preferable, and alkali metal chlorides are most preferable.

The conversion into a salt soluble in an organic solvent and/or water may be carried out as follows. Thus, in the case of using an acidic aqueous solution containing 3-amino-2-hydroxypropionic acid derivative (1) and an acid (i.e. in the case of using an acid for hydrolysis in the third step), neutralization may be carried out using a basic compound, for example, hydroxides such as lithium hydroxide or sodium hydroxide; or carbonates such as lithium carbonate, sodium carbonate or sodium bicarbonate. On the other hand, in the case of using a basic aqueous solution containing 3-amino-2-hydroxypropionic acid derivative (1) and a base (i.e. in the case of using a base for hydrolysis in the third step), a basic compound, for example, hydroxides such as lithium hydroxide or sodium hydroxide; or carbonates such as lithium carbonate, sodium carbonate or sodium bicarbonate may be used as a base, and neutralization may be carried out using an acid after completion of the above hydrolysis. The acid used for the above hydrolysis or neutralization is not limited to a particular one if its salt with the above basic compound is soluble in the above organic solvent and/or water. For example, inorganic acids such as hydrohalogenic acids (e.g. hydrochloric acid), sulfuric acid, sulfurous acid or phosphoric acid; organic acids such as methanesulfonic acid or trifluoroacetic acid may be used. Hydrohalogenic acids are preferable and hydrochloric acid is particularly preferable.

In this connection, 3-amino-2-hydroxypropionic acid derivatives (1) may be water-soluble compounds. Accordingly, it may be difficult to efficiently precipitate 3-amino-2-hydroxypropionic acid derivatives (1), with retaining a salt formed by neutralization of a coexisting acid or base in mother liquor. In such a case, it is effective to adopt a process for minimizing the precipitating amount of a salt formed by the above neutralization, by coexistence of a water-soluble organic solvent, in particular, an organic solvent miscible with water in the above medium, and by selection of the above salt soluble in an organic solvent and water as a salt formed by the above neutralization. Thus, it is effective to adopt a process for converting an acid or a base coexisting in an aqueous solution obtained in the above third step [step of converting substituted-3-amino-2-hydroxypropionic acid derivatives (4) into 3-amino-2-hydroxypropionic acid derivatives (1)] into a salt soluble in an organic solvent and water by neutralization.

The above salt soluble in an organic solvent and water is not limited to a particular one, and preferably includes lithium salts, and more preferably lithium halide salts such as lithium chloride or lithium bromide.

The above conversion into a salt soluble in an organic solvent and water may be carried out as follows. Thus, in the case of using an acidic aqueous solution containing 3-amino-2-hydroxypropionic acid derivative (1) and an acid (i.e. in the case of using an acid for hydrolysis in the third step), neutralization may be carried out using a basic lithium compound such as lithium hydroxide and lithium carbonate. On the other hand, in the case of using a basic aqueous solution containing 3-amino-2-hydroxypropionic acid derivative (1) and a base (i.e. in the case of using a base for hydrolysis in the third step), a basic lithium compound such as lithium hydroxide and lithium carbonate may be used as a base, and neutralization may be carried out using an acid after completion of the above hydrolysis. The acid used for the above hydrolysis or neutralization is not limited to a particular one if its salt with the above lithium compound is soluble in the above organic solvent and water. For example, inorganic acids such as hydrohalogenic acids (e.g. hydrochloric acid), sulfuric acid, sulfurous acid or phosphoric acid; organic acids such as methanesulfonic acid or trifluoroacetic acid may be used. Hydrohalogenic acids are preferable and hydrochloric acid is particularly preferable.

The above medium used in the conversion into a salt soluble in an organic solvent and/or water is not limited to a particular one. Since, however, it is generally suitable to carry out the above conversion into a salt in the presence of water, water is usually used. Also, an excess amount of water is generally used for hydrolysis in the third step, and therefore, water is preferably used. The amount of water used is not limited to a particular range. Since, however, the above 3-amino-2-hydroxypropionic acid derivatives (1) may be water-soluble compounds, it is preferable to minimize the amount of water from the viewpoint of increasing the precipitating amount of the derivatives. In general, the amount of water is adjusted by the amount of water used in the above hydrolysis. If necessary, water may be distilled off after completion of the hydrolysis.

Also, it is effective to decrease the amount of water-soluble 3-amino-2-hydroxypropionic acid derivatives (1) dissolved and increase the amount precipitated, by coexistence of an organic solvent water-soluble, in particular, miscible with water, which has a low solubility of 3-amino-2-hydroxypropionic acid derivatives (1), in the above medium. The amount of the above organic solvent used can not be defined uniformly and is usually 0 to 20-fold by weight, preferably 0.1 to 10-fold by weight, and more preferably 0.2 to 5-fold by weight, relative to the water. In this connection, the above medium may form a homogeneous phase or a multiphase system separating into two or more phases, and may be freely selected in a range of not affecting the step.

Preferable examples of the above organic solvent include, for example, ethers such as tetrahydrofuran, 1,4-dioxane or t-butyl methyl ether; ketones such as acetone, methyl ethyl ketone or cyclohexanone; alcohols such as methanol, ethanol, isopropanol or benzyl alcohol. Among others, organic solvents miscible with water are particularly preferable. Among the organic solvents miscible with water, tetrahydrofuran or 1,4-dioxane is a particularly preferable ether, acetone is a particularly preferable ketone, and methanol or ethanol is a particularly preferable alcohol. These solvents may be used alone or in a mixture of two or more solvents. Of course, the use of these organic solvents includes the case wherein an organic solvent used in the previous step is used as it is without any solvent-replacement. Also, these organic solvents may be newly added in order to increase the precipitating amount of 3-amino-2-hydroxypropionic acid derivatives (1), after carrying out the above conversion into a salt soluble in an organic solvent and/or water.

When precipitating 3-amino-2-hydroxypropionic acid derivatives (1), a neutralizing treatment is carried out for an aqueous solution after completion of the above hydrolysis, in order to convert a coexisting acid or base into the above soluble salt. If, however, the aqueous solution has a poor fluidity due to a small amount of water, for example, it is preferable to add water up to a water amount necessary for fluidizing and preferably dissolving the above aqueous solution, before carrying out the above neutralizing treatment. Also, if necessary, filtration of insoluble matters, treatment by an adsorbent such as activated charcoal, washing of the aqueous solution by an organic solvent immiscible with water or the like may be carried out for the purpose of removing impurities or decolorizing.

Preferably, the above neutralizing treatment may be carried out by adjusting the aqueous solution to a weakly acidic to neutral range, in particular, to around isoelectric point of the above 3-amino-2-hydroxypropionic acid derivatives (1). The range can not be defined uniformly, depending on the kind of the 3-amino-2-hydroxypropionic acid derivatives (1), and usually, it is preferably adjusted to around pH 4 to 7.

In the above neutralizing treatment, addition of an acid or a base over a longer period generally tends to increase fluid and separation properties of a slurry for crystallization as well as effects of purification. Accordingly, the acid or base is preferably added over a maximumly long period, in a range not affecting from the viewpoint of productivity. Furthermore, if necessary, a water-soluble organic solvent may be added to the slurry for crystallization thus obtained, as described above. Besides, any procedures to increase a precipitating amount which are used in coventional crystallization procedures, for example, cooling may be used without any limitation.

The 3-amino-2-hydroxypropionic acid derivatives (1) precipitated may be separated using conventional solid-liquid separation procedures such as filtration, centrifugation or the like. Also, wet solids of the 3-amino-2-hydroxypropionic acid derivatives (1) separated may be washed using, for example, the above water-soluble organic solvent or a mixed solvent of the above water-soluble organic solvent and water, and then, the solvent may be removed at atmospheric pressure or under reduced pressure.

Next described is a process for preparing the N-protected-3-amino-2-hydroxypropionic acid derivatives (2) used in the process according to the present invention. The process for preparing the N-protected-3-amino-2-hydroxypropionic acid derivatives (2) is not limited to a particular one and various processes may be used (including processes exemplified as those in the prior art). Of these processes, it is preferable to use processes suitable for industrial production for the purpose of the present invention.

For example (e.g. JP-A-10/59909), dihaloketone derivatives [hereinafter, also referred to as dihaloketone derivatives (5)] represented by the following general formula (5):

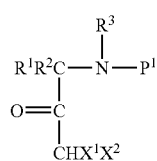

(5)

wherein $R^1$, $R^2$ and $R^3$ are as defined above;
$P^1$ represents a hydrogen atom or a protecting group for an amino group; and
$X^1$ and $X^2$, independently from each other, represent a halogen atom;

may be hydrolyzed to convert into 3-amino-2-hydroxypropionic acid derivatives [hereinafter, also referred to as 3-amino-2-hydroxypropionic acid derivatives (6)] represented by the following general formula (6):

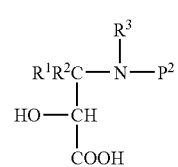

(6)

wherein $R^1$, $R^2$ and $R^3$ are as defined above; and
$P^2$ represents a hydrogen atom or the above $P^1$.

The above protecting group of an amino group represented by $P^1$ and $P^2$ is not limited to a particular one and may be selected from the protecting groups as described, for example, in PROTECTIVE GROUPS IN ORGANIC SYNTHESIS, 2nd ed., JOHN WILLY & SONS publ. (1991). Specific examples include, for example, urethane-type protecting groups, acyl-type protecting groups and alkyl-type protecting groups. In general, from the viewpoint of an easy handling, an inexpensiveness, a convenient synthesis of substrate compounds and the like, urethane-type protecting groups are preferably used.

In this case, it is most preferable to carry out the above hydrolysis in dihaloketone derivatives (5) wherein $P^1$ is a urethane-type protecting group (i.e. $P^1=S^1$), with retaining the protecting group $P^1$, to produce 3-amino-2-hydroxypropionic acid derivatives (6) wherein $P^2$ is $P^1$ [corresponding to N-protected-3-amino-2-hydroxypropionic acid derivatives (2) wherein $S^2$ is a hydrogen atom]. It is also preferable to carry out deprotection in addition to hydrolysis in dihaloketone derivatives (5) wherein $P^1$ is a urethane-type protecting group (i.e. $P^1=S^1$) under the above hydrolysis conditions to produce 3-amino-2-hydroxypropionic acid derivatives (6) wherein $P^2$ is a hydrogen atom, after which a urethane-type protecting group is introduced into an amino group in the later derivatives to convert into N-protected-3-amino-2-hydroxypropionic acid derivatives (2) wherein $S^2$ is a hydrogen atom.

If the above process for preparing 3-amino-2-hydroxypropionic acid derivatives (6) by hydrolysis of dihaloketone derivatives (5) is used and if esterification is not carried out separately, N-protected-3-amino-2-hydroxypropionic acid derivatives (2) wherein $S^2$ is a hydrogen atom are obtained in general. Accordingly, if N-protected-3-amino-2-hydroxypropionic acid derivatives (2) wherein $S^2$ is an ester residue are desired, esterification may be carried out using a known esterification method.

In this connection, it is necessary to convert $P^1$ and/or $P^2$ ultimately into a urethane-type protecting group for an amino group in the above process, except for the case where $S^1=P^1=P^2=$urethane-type protecting group. In this case, it is usually necessary to convert $P^1$ and/or $P^2$ into a urethane-type protecting group by the action of an amino-protecting agent for introducing a urethane-type protecting group for an amino group, after conversion of $P^1$ or $P^2$ into a hydrogen atom by deprotection if $P^1$ or $P^2$ is a protecting group for an amino group, and using $P^1$ and $P^2$ as they are if $P^1$ and $P^2$ are a hydrogen atom, respectively.

The above methods for deprotecting and for introducing a urethane-type protecting group are not limited to particular ones and include, for example, those described in PROTECTIVE GROUPS IN ORGANIC SYNTHESIS, 2nd ed., JOHN WILLY & SONS publ. (1991). For example, the above method for deprotecting includes acid treatment, base treatment (alkali treatment), catalytic reduction, electrolytic reduction, Zn/AcOH treatment, treatment with a thiol compound or the like, although a suitable method varies depending on the kind of the protecting group. Also, the above method for introducing a urethane-type protecting group is not limited to a particular one and generally includes, for example, a method of introducing a methoxycarbonyl group, an ethoxycarbonyl group or a benzyloxycarbonyl group by treatment using chloroformic esters such as methyl chloroformate, ethyl chloroformate or benzyl chloroformate as an amino-protecting agent, or a method of introducing a tert-butoxycarbonyl group by treatment using dicarbonates such as di-tert-butyl dicarbonate as an amino-protecting agent As described above, N-protected-3-amino-2-hydroxypropionic acid derivatives (2) may be obtained by hydrolyzing dihaloketone derivatives (5) to convert into 3-amino-2-hydroxypropionic acid derivatives (6), and if necessary, by further converting $P^1$ or $P^2$ into $S^1$ and/or by further esterifying 3-amino-2-hydroxypropionic acid derivatives (6).

The above dihaloketone derivatives (5) may be prepared by various processes. For example, they may be prepared from amino acid derivatives [hereinafter, also referred to as amino acid derivatives (10)] represented by the following general formula (10):

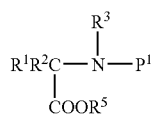

(10)

wherein $R^1$, $R^2$, $R^3$ and $P^1$ are as defined above; and $R^5$ represents a hydrogen atom or an ester residue.

The processes include, for example, a process comprising reacting amino acid ester derivative (10) wherein $R^5$ is an ester residue with a monohaloacetic acid derivative to obtain a monohaloketone derivative and then treating the later derivative with a halogenating agent (JP-A-10/59909), or a process comprising reacting amino acid ester derivative (10) wherein $R^5$ is an ester residue with a dihalomethane (JP Application No. 11/63478).

In the meantime, N-protected-3-amino-2-hydroxypropionic acid derivatives (2) prepared by a prior art process, in particular derivatives (2) having $R^1$ and $R^2$ different from each other usually contain an isomer having a reverse steric configuration at 2-position carbon in a not small amount. In many cases, they are obtained as a mixture of diastereomers having the same steric configuration at 3-position carbon and having a different steric configuration only at 2-position carbon [i.e. a mixture of (2S,3S)-isomer and (2R,3S)-isomer, or a mixture of (2S,3R)-isomer and (2R,3R)-isomer]. For example, the derivatives (2) wherein $R^1$ is a substituted or unsubstituted alkyl group having 1 to 30 carbon atoms, a substituted or unsubstituted aryl group having 6 to 30 carbon atoms, or a substituted or unsubstituted aralkyl group having 7 to 30 carbon atoms, and $R^2$ is a hydrogen atom are obtained as a mixture of diastereomers having an erythro configuration and a threo configuration [i.e. a mixture of (2S,3S)-isomer and (2R,3S)-isomer, or a mixture of (2R,3R)-isomer and (2S,3R)-isomer].

In this connection, the steric expressions [erythro] and [threo] mean a relative steric configuration represented by the following formulae (11) and (12), respectively, using Fischer projection formula:

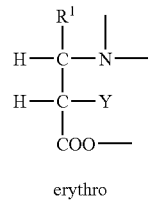

(11)

erythro

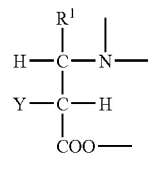

(12)

threo wherein $R^1$ is as defined above; and

Y represents an oxygen atom or leaving group L wherein L is as defined above.

In an industrial production process of desired stereoisomeric 3-amino-2-hydroxypropionic acid derivatives (1), the above mixture of diastereomers is not preferable, and usually, undesired diastereomers have to be removed by various purification procedures such as crystallization, distillation, chromatography or the like. It is often difficult to remove the above undesired diastereomers efficiently (in a good yield) by purification. In addition, there is usually no other way but to dispose of the undesired diastereomers removed unless they have any application fields, and therefore, they are responsible for a very low yield.

However, the present inventors found, for example, as shown in the following scheme that, in the above second step wherein N-protected-3-aminopropionic acid derivative (3) having an erythro configuration [hereinafter, also referred to as erythro-isomer (3)] is converted into substituted-3-amino-2-hydroxypropionic acid derivative (4) having a threo configuration [hereinafter, also referred to as threo-isomer (4)], it is possible to retain N-protected-3-aminopropionic acid derivative (3) having a threo configuration [hereinafter, also referred to as threo-isomer (3)] which is contained in erythro-isomer (3) and has no need to invert, as it is unreacted, by selecting reaction conditions suitably. In addition, they also found that retained threo-isomer (3) can be supplied to conversion of leaving group L into a hydroxyl group as well as to deprotection of an amino-protecting group, with retaining its steric configuration, under reaction conditions of the above third step followed:

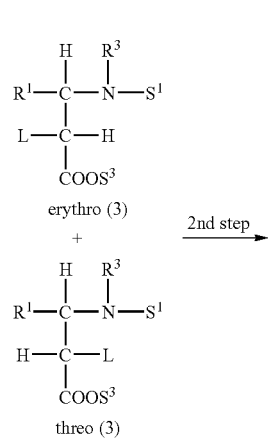

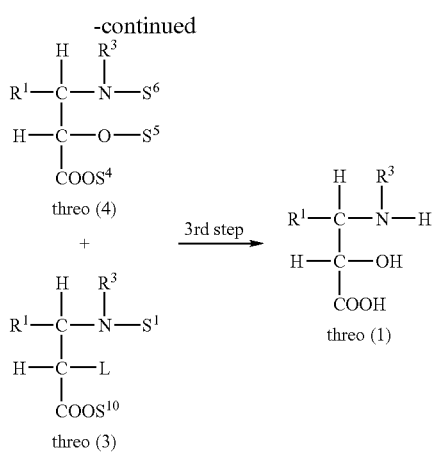

wherein $R^1$, $R^2$, $R^3$, $S^1$, $S^3$, $S^4$, $S^5$, $S^6$ and L are as defined above; and $S^{10}$ represents a hydrogen atom or an ester residue.

Thus, if a mixture of erythro-isomer (3) and threo-isomer (3) is used, it is possible to convert erythro-isomer (3) selectively into threo-isomer (4) having an inverted steric configuration at 2-position carbon, and at the same time, to retain threo-isomer (3) as it is, in the second step, as shown in the above scheme. Subsequently, in the third step, leaving group L of retained threo-isomer (3) may be converted into a hydroxyl group to obtain threo-isomer (4), and then, substituents may be removed to obtain 3-amino-2-hydroxypropionic acid derivative (1) having a threo configuration [hereinafter, also referred to as threo-isomer (1)]. This process can greatly increase the diastereomer excess of the products.

In the above process, $R^1$ is a substituted or unsubstituted alkyl group having 1 to 30 carbon atoms, a substituted or unsubstituted aryl group having 6 to 30 carbon atoms, or a substituted or unsubstituted aralkyl group having 7 to 30 carbon atoms, and $R^2$ is a hydrogen atom. However, $R^1$ is preferably a substituted or unsubstituted aralkyl group having 7 to 30 carbon atoms, more preferably a substituted or unsubstituted benzyl group, and most preferably an unsubstituted benzyl group. Also, leaving group L is preferably the above sulfonyloxy group.

In the above process, in order to convert erythro-isomer (3) into threo-isomer (4) having an inverted steric configuration at 2-position carbon, and at the same time, to retain threo-isomer (3) as it is, it is preferable to carry out the reaction in the above second step under mild conditions, for example, by using an acidic substance or a basic substance in a small amount, by retaining a low reaction temperature or by combining these conditions. As the conditions become mild, it is possible to retain threo-isomer (3) efficiently.

The above acidic substance is not limited to a particular one and may be selected from acidic substances used in the above second step. The amount of the acidic substances used varies depending on the kind of acids, and they are usually used in a molar amount below 5-fold, preferably in a molar amount below 2-fold, and more preferably in a molar amount below 1-fold, relative to the total amount of erythro-isomer (3) and threo-isomer (3).

The above basic substance is not limited to a particular one and weakly basic substances used in the above second step are preferably used. Among others, N,N-dimethyl formamide, pyridine or the like may be used preferably. The amount of the above basic substances used varies depending on the kind of bases, and they are usually used in a molar amount below 50-fold, preferably in a molar amount below 20-fold, and more preferably in a molar amount below 10-fold, relative to the total amount of erythro-isomer (3) and threo-isomer (3).

Also, the reaction temperature varies, for example, depending on the kind of the above acidic substances or basic substances, the amount of them used and the like, and it may be usually below 120° C., preferably below 100° C., and more preferably below 80° C.

Reaction solvents used in this reaction are not limited to particular ones and, various organic solvents used in the above second step may be used. Examples of the reaction solvents include, for example, aliphatic hydrocarbons such as hexane, heptane or methylcyclohexane; aromatic hydrocarbons such as toluene or xylene; halogenated hydrocarbons such as methylene chloride or chloroform; ethers such as tetrahydrofuran, 1,4-dioxane or t-butyl methyl ether; aliphatic acid esters such as methyl acetate, ethyl acetate or isopropyl acetate; nitriles such as acetonitrile; alcohols such as methanol, ethanol, isopropanol or benzyl alcohol. Toluene is a particularly preferable aromatic hydrocarbon, 1,4-dioxane is a particularly preferable ether, and ethyl acetate is a particularly preferable aliphatic acid ester. Among others, aromatic hydrocarbons are preferably used. These organic solvents may be used alone or in a mixture of two or more solvents. Besides, if the basic substances used in the above second step are liquid at the above reaction temperature, the above basic substances may be used so as to also serve as a reaction solvent.

By the above process, it is possible to obtain 3-amino-2-hydroxy-4-phenylbutyric acid wherein the diastereomer excess of the threo-isomer is 87% d.e. from N-ethoxycarbonyl-3-amino-2-methanesulfonyloxy-4-phenylbutyric acid methyl ester [in the above general formula (2), $R^1$=benzyl group, $R^2$=hydrogen atom, $P^1$=ethoxycarbonyl group, and $R^4$=methyl group] wherein the diastereomer excess of the erythro-isomer is 66% d.e., for example, as shown in Example 9 below. Thus, the process can greatly increase the diastereomer excess.

As described above, according to the present invention, it is possible to prepare conveniently and efficiently, and with industrial advantages, 3-amino-2-hydroxypropionic acid derivatives (1) having a particular steric configuration from N-protected-3-amino-2-hydroxypropionic acid derivatives (2) having a reverse steric configuration at 2-position carbon.

EXAMPLES

The present invention is illustrated in more detail based on the following examples, but it is not limited thereto.

Example 1

Synthesis of (2S,3S)-3-(ethoxycarbonyl)amino-2-hydroxy-4-phenylbutyric acid (erythro-isomer)

A toluene solution (677.2 g) containing (S)-1,1-dibromo-3-(ethoxycarbonyl)amino-2-oxo-4-phenylbutane (67.65 g) was added dropwise to a 10% aqueous solution of sodium hydroxide (691.3 g) ice-cooled over 10 hours, and stirred at the same temperature for 1 hour. The resultant reaction solution was further reacted at 60° C. for 6 hours. The organic phase was separated from the resultant reaction mixture, ethyl acetate (400 ml) was added to the resultant aqueous phase, and the pH was adjusted to pH 2 with conc. hydrochloric acid (150 g). The organic phase was separated to obtain an aqueous solution (944.7 g) containing erythro-3-amino-2-hydroxy-4-phenylbutyric acid (26.52 g) and threo-3-amino-2-hydroxy-4-phenylbutyric acid (5.44 g). The ratio of erythro-isomer/threo-isomer was 83/17, and the diastereomer excess was 66% d.e.

The aqueous solution (940.4 g) [containing erythro-3-amino-2-hydroxy-4-phenylbutyric acid (26.40 g) and threo-3-amino-2-hydroxy-4-phenylbutyric acid (5.42 g)] thus obtained was adjusted to pH 10 with a 30% aqueous solution of sodium hydroxide (91 g) under ice-cooling. While the aqueous solution was maintaind at an internal temperature below 5° C. and at around pH 10 with a 30% aqueous solution of sodium hydroxide, ethyl chloroformate (19.52 g) was added dropwise to the solution over 3 hours. The mixture was further stirred at the same temperature for 1 hour to continue the reaction. The reaction solution was warmed to room temperature and washed with toluene (64 ml). Then, ethyl acetate (849.3 ml) was added to the solution, the pH was adjusted to pH 2 with conc. hydrochloric acid (60 g), and the aqueous phase was separated. Then, the resultant organic phase was washed with water (96 ml) to obtain an ethyl acetate extract (971.9 g). Determination by HPLC revealed that the amount of the diastereomer mixture of 3-(ethoxycarbonyl)amino-2-hydroxy-4-phenylbutyric acid in the resultant extract was 43.07 g calculated as an erythro-isomer. Also, the HPLC area ratio of erythro-isomer/threo-isomer was 83/17, and the diastereomer excess was 66% d.e.

The ethyl acetate extract (870.3 g) thus obtained [containing a diastereomer mixture (38.57 g) of 3-(ethoxycarbonyl)amino-2-hydroxy-4-phenylbutyric acid] was concentrated under reduced pressure, and solvent-replacement was then carried out with toluene to precipitate crystals. The total amount of the concentrate was adjusted to 770.5 g, acetonitrile (118.3 g) was then added to the mixture, and the mixture was heated to 70° C. to completely dissolve the crystals. After maintaining the mixture at the same temperature for 1 or more hours, cooling crystallization was carried out at a cooling rate of 10° C./hour, and precipitated crystals were separated by suction filtration. The crystals were washed with cold toluene (200 ml) and then dried in vacuo to obtain white crystals (30.23 g). The purity of (2S,3S)-3-(ethoxycarbonyl)amino-2-hydroxy-4-phenylbutyric acid (erythro-isomer) was 99% by weight. The HPLC area ratio of erythro-isomer/threo-isomer was 99/1, and the diastereomer excess was 99% d.e. (2R,3R)-Isomer (enantiomer) was not detected.

Example 2

Synthesis of a diastereomer mixture of 3-(ethoxycarbonyl)amino-2-hydroxy-4-phenylbutyric acid The ethyl acetate extract (96.5 g) obtained in Example 1 [containing a diastereomer mixture (4.28 g) of 3-(ethoxycarbonyl)amino-2-hydroxy-4-phenylbutyric acid] was concentrated to dry up under reduced pressure. The solid was ground in a porcelain mortar and then further dried in vacuo to obtain a powdery solid (4.43 g). The purity of erythro-3-(ethoxycarbonyl)amino-2-hydroxy-4-phenylbutyric acid was 80% by weight. Also, the HPLC area ratio of erythro-isomer/threo-isomer was 83/17, and the diastereomer excess was 66% d.e.

Example 3

Synthesis of (2S,3S)-3-(t-butoxycarbonyl)amino-2-hydroxy-4-phenylbutyric acid (erythro-isomer)

(S)-1,1-Dibromo-3-(t-butoxycarbonyl)amino-2-oxo-4-phenylbutane (42.12 g) was suspended in toluene (420 ml) and water (280 ml) and the suspension was ice-cooled. To this suspension, a 30% aqueous solution of sodium hydroxide (133 g) was added dropwise over 1 hour, and the mixture was stirred at the same temperature for 20 hours. The organic phase was separated from the resultant reaction mixture, ethyl acetate (600 ml) was added to the resultant aqueous phase, the pH was adjusted to pH 2 with conc. hydrochloric acid (115 g), and the aqueous phase was separated. Then, the resultant organic phase was washed with water (70 ml) to obtain an ethyl acetate extract (591.9 g). Determination by HPLC revealed that the amount of the diastereomer mixture of 3-(t-butoxycarbonyl)amino-2-hydroxy-4-phenylbutyric acid in the resultant extract was 27.14 g calculated as an erythro-isomer. Also, the HPLC area ratio of erythro-isomer/threo-isomer was 83/17, and the diastereomer excess was 66% d.e.

The extract (589.2 g) [containing a diastereomer mixture (27.02 g) of 3-(t-butoxycarbonyl)amino-2-hydroxy-4-phenylbutyric acid] was concentrated under reduced pressure, and solvent-replacement was then carried out with toluene to precipitate crystals. The total amount of the concentrate was adjusted to 544.5 g, acetonitrile (120.3 g) was then added to the mixture, and the mixture was heated to 70° C. to completely dissolve the crystals. After maintaining the mixture at the same temperature for 1 hour, crystallization was carried out by cooling the mixture to -10° C. at a cooling rate of 2.5° C./hour, and precipitated crystals were separated by suction filtration. The crystals were washed with cold toluene (150 ml) and then dried in vacuo to obtain white crystals (20.23 g). The purity of (2S,3S)-3-(t-butoxycarbonyl)amino-2-hydroxy-4-phenylbutyric acid was 99% by weight. The HPLC area ratio of erythro-isomer/threo-isomer was 99/1, and the diastereomer excess was 99% d.e. (2R, 3R)-Isomer (enantiomer) was not detected.

Example 4

Conversion of (2S,3S)-3-(ethoxycarbonyl)amino-2-hydroxy-4-phenylbutyric acid into (2S,3S)-3-(ethoxycarbonyl)-amino-2-methanesulfonyloxy-4-phenylbutyric acid methyl ester Thionyl chloride (596 mg) was added to methanol (1.39 g) over 10 minutes under ice-cooling, and the mixture was reacted at the same temperature for 1 hour. The resultant solution was added to a solution of (2S,3S)-3-(ethoxycarbonyl)amino-2-hydroxy-4-phenylbutyric acid (HPLC area ratio of erythro-isomer/threo-isomer=99/1) (1.04 g) and toluene (10 ml) over 10 minutes under ice-cooling. The mixture was reacted at the same temperature for 2 hours and then warmed to room temperature. From the resultant reaction solution, methanol and thionyl chloride as well as components secondarily produced from these reagents and having a low boiling point such as sulfurous acid, hydrogen chloride or the like were distilled off under reduced pressure. Tetrahydrofuran was added to the resultant residue to obtain a tetrahydrofuran solution (10.12 g) of (2S,3S)-3-(ethoxycarbonyl)amino-2-hydroxy-4-phenylbutyric acid methyl ester. The HPLC area ratio of erythro-isomer/threo-isomer was 99/1, and the diastereomer excess was 99% d.e.

To the tetrahydrofuran solution (5.04 g) of (2S,3S)-3-(ethoxycarbonyl)amino-2-hydroxy-4-phenylbutyric acid methyl ester thus obtained, triethylamine (421 mg) was added under ice-cooling. Then, methanesulfony chloride (1376 mg) was added to the mixture over 10 minutes, and the mixture was reacted at the same temperature for 2 hours. Toluene (5 ml) and water (5 ml) were added to the resultant reaction solution, and the aqueous phase was separated. The resultant organic phase was concentrated under reduced pressure to obtain (2S,3S)-3-(ethoxycarbonyl)amino-2-methanesulfonyloxy-4-phenylbutyric acid methyl ester (erythro-isomer) (685 mg) as a white solid. The HPLC area ratio of erythro-isomer/threo-isomer was 99/1, and the diastereomer excess was 99% d.e.

$^1$H-NMR Spectra (CDCl$_3$, TMS internal standard) of the resultant (2S,3S)-3-(ethoxycarbonyl)amino-2-methanesulfonyloxy-4-phenylbutyric acid methyl ester were: δ 1.19 (3H, t, J=7.2 Hz), 2.79–2.86 (2H, m), 3.20 (3H, s), 3.64 (3H, s), 4.08 (2H, q, J=7.2 Hz), 4.55–4.63 (1H, m), 4.92 (1H, d, J=8.8 Hz), 5.31 (1H, brs), 7.17–7.33 (5H, m).

Also, $^{13}$C NMR spectra (CDCl$_3$) were: δ 14.4, 35.6, 39.2, 52.8, 53.0, 61.3, 78.6, 127.1, 128.6, 129.3, 135.9, 155.8, 167.4.

Example 5

Conversion of (2S,3S)-3-(ethoxycarbonyl)amino-2-methanesulfonyloxy-4-phenylbutyric acid methyl ester into (2R,3S)-3-amino-2-hydroxy-4-phenylbutyric acid (2S,3S)-3-(Ethoxycarbonyl)amino-2-methanesulfonyloxy-4-phenylbutyric acid methyl ester (HPLC area ratio of erythro-isomer/threo-isomer=99/1) (148 mg) obtained in Example 4 was dissolved in N,N-dimethyl formamide (3 ml), the temperature of the mixture was gradually raised from 60° C., and the mixture was reacted finally at 100° C. for 8 hours. The resultant reaction solution was concentrated under reduced pressure, water (2 ml) and a 30% aqueous solution of sodium hydroxide (551 mg) were added to the resultant residue, and the mixture was reacted at 60° C. for 15 hours. Determination by HPLC revealed that the amount of (2R,3S)-3-amino-2-hydroxy-4-phenylbutyric acid (threo-isomer) in the resultant reaction solution was 71 mg. Also, (2S,3S)-3-amino-2-hydroxy-4-phenylbutyric acid (erythro-isomer) was not detected.

Example 6

Conversion of (2S,3S)-3-(ethoxycarbonyl)amino-2-hydroxy-4-phenylbutyric acid through 3-(ethoxycarbonyl)amino-2-chloro-4-phenylbutyric acid into (2R,3S)-3-amino-2-hydroxy-4-phenylbutyric acid Thionyl chloride (694 mg) was added to a solution of (2S,3S)-3-(ethoxycarbonyl)amino-2-hydroxy-4-phenylbutyric acid (HPLC area ratio of erythro-isomer/threo-isomer=99/1) (277 mg) and tetrahydrofuran (2 ml) over 2 hours under ice-cooling, and the temperature of the mixture was then raised to 60° C. stepwise. The mixture was reacted at 60° C. for 24 hours. From the resultant reaction solution, tetrahydrofuran and thionyl chloride as well as components secondarily produced from thionyl chloride and having a low boiling point such as sulfurous acid, hydrogen chloride or the like were distlled off under reduced pressure. The resultant residue was treated with a silica gel column (silica gel: WAKOGEL C-200, developing solvent: ethyl acetate/hexane=30/70) to obtain a concentrate (100 mg) of 3-(ethoxycarbonyl)amino-2-chloro-4-phenylbutyric acid as a solid.

LC/MS Spectra (ESI) of the resultant 3-(ethoxycarbonyl)amino-2-chloro-4-phenylbutyric acid were: m/e 286.1 [100%, M(Cl$^{35}$)+1], 288.2 [36%, M(Cl$^{37}$)+1].

The concentrate (73 mg) thus obtained was dissolved in N,N-dimethyl formamide (1 ml), and the mixture was reacted at 100° C. for 2 days. The resultant reaction solution was concentrated under reduced pressure, water (0.4 ml) and a 30% aqueous solution of sodium hydroxide (0.4 ml) were added to the resultant residue, and the mixture was reacted at 60° C. for 18 hours. Determination by HPLC revealed that the amount of the (2R,3S)-3-amino-2-hydroxy-4-phenylbutyric acid in the resultant reaction solution was 46 mg. Also, the HPLC area ratio of threo-isomer/erythro-isomer was 97/3, and the diastereomer excess was 94% d.e.

Example 7

Conversion of 3-(ethoxycarbonyl)amino-2-hydroxy-4-phenylbutyric acid (diastereomer mixture) into 3-(ethoxycarbonyl)-amino-2-methanesulfonyloxy-4-phenylbutyric acid methyl ester Thionyl chloride (3.46 g) was added to methanol (2.64 g) over 30 minutes under ice-cooling, and the mixture was reacted at the same temperature for 1 hour. The resultant solution was added to a toluene solution (54.51 g) containing the diastereomer mixture (4.05 g) of 3-(ethoxycarbonyl)amino-2-hydroxy-4-phenylbutyric acid obtained in Example 2 (HPLC area ratio of erythro-isomer/threo-isomer=83/17, diastereomer excess=66% d.e.) over 30 minutes under ice-cooling. The mixture was reacted at the same temperature for 2 hours, and the temperature of the mixture was then raised to room temperature. From the resultant reaction solution, methanol and thionyl chloride as well as components secondarily produced from these reagents and having a low boiling point such as sulfurous acid, hydrogen chloride or the like were distilled off under reduced pressure. Toluene (90 ml) was added to the resultant residue and water (30 ml) was then added to the mixture with ice-cooling. At this point, the pH of the aqueous phase was about pH 0. The pH was adjusted to pH 5 with a 30% aqueous solution of sodium hydroxide, and the aqueous phase was separated to obtain an extract (82.64 g) of 3-(ethoxycarbonyl)amino-2-hydroxy-4-phenylbutyric acid methyl ester.

The extract (75.38 g) of 3-(ethoxycarbonyl)amino-2-hydroxy-4-phenylbutyric acid methyl ester thus obtained was concentrated under reduced pressure to obtain a concentrate (30.27 g). Triethylamine (2.31 g) was added to the concentrate under ice-cooling, and methanesulfonyl chloride (1.91 g) was then added to the mixture over 30 minutes. The mixture was reacted at the same temperature for 1 hour. To the resultant reaction solution, water (30 ml) and ethyl acetate (30 ml) were added. At this point, the pH of the aqueous phase was pH 9.1. The pH was adjusted to pH 4.7 with conc. hydrochloric acid, and the aqueous phase was separated to obtain an organic phase. Furthermore, the aqueous phase was extracted with ethyl acetate (30 ml), and the resultant organic phase was collected together with the previous organic phase. The organic phase was concentrated under reduced pressure, and solvent-replacement was then carried out to obtain an ethyl acetate solution (25.76 g) of 3-(ethoxycarbonyl)amino-2-methanesulfonyloxy-4-phenylbutyric acid methyl ester. Determination by HPLC revealed that the amount of the diastereomer mixture of 3-(ethoxycarbonyl)amino-2-methanesulfonyloxy-4-phenylbutyric acid methyl ester in the resultant solution was 4.67 g calculated as an erythro-isomer. Also, the HPLC area ratio of erythro-isomer/threo-isomer was 83/17, and the diastereomer excess was 66% d.e.

Example 8

Conversion of 3-(ethoxycarbonyl)amino-2-methanesulfonyloxy-4-phenylbutyric acid methyl ester into 4-benzyl-2-oxazolidinone-5-carboxylic acid methyl ester The ethyl acetate solution (833 mg) of the diastereomer mixture of 3-(ethoxycarbonyl)amino-2-methanesulfonyloxy-4-phenylbutyric acid methyl ester obtained in Example 7 [corresponding to diastereomer mixture (151 mg) of 3-(ethoxycarbonyl)amino-2-methanesulfonyloxy-4-phenylbutyric acid methyl ester, calculated as an erythro-isomer; HPLC area ratio of erythro-isomer/threo-isomer=83/17] was solvent-replaced with toluene to obtain a toluene solution (901 mg). N,N-Dimethyl formamide (1 ml) was added to the solution, and the mixture was reacted at 80° C. for 20 hours, at 100° C. for 6 hours, and further at 110° C. for 25 hours. The resultant reaction solution was concentrated under reduced pressure, ethyl acetate (3 ml) was added to the resultant residue, and the mixture was washed with water (0.5 ml) for three times. The resultant organic phase was concentrated under reduced pressure to obtain 4-benzyl-2-oxazolidinone-5-carboxylic acid methyl ester (99 mg) as an oily substance. The HPLC area ratio of threo-isomer/erythro-isomer was 83/17, and the diastereomer excess was 66% d.e.

$^1$H-NMR Spectra (CDCl$_3$, TMS internal standard) of the resultant threo-4-benzyl-2-oxazolidinone-5-carboxylic acid methyl ester were: δ 2.79 (1H, dd, CH$_2$Ph, J=13.2 Hz (CH$_2$Ph), 10 Hz (H-4)), 3.07 (1H, dd, CH$_2$Ph, J=13.2 Hz (CH$_2$Ph), 4.4 Hz (H-4)), 3.86 (3H, s, CO$_2$CH$_3$), 4.01–4.09 (1H, m, H-4), 4.72 (1H, d, H-5, J=4.4 Hz (H-4)), 7.15–7.38 (5H, m, Ph).

Also, $^1$H-NMR spectra (CDCl$_3$, TMS internal standard) of erythro-4-benzyl-2-oxazolidinone-5-carboxylic acid methyl ester were: δ 2.54 (1H, dd, CH$_2$Ph, J=13.2 Hz (CH$_2$Ph), 12 Hz (H-4)), 2.94 (1H, dd, CH$_2$Ph, J=13.2 Hz (CH$_2$Ph), 3.2 Hz (H-4)), 3.86 (3H, s, CO$_2$CH$_3$), 4.26–4.34 (1H, m, H-4), 5.17 (1H, d, H-5, J=8.4 Hz (H-4)), 7.15–7.38 (5H, m, Ph).

Example 9

Conversion of 3-(ethoxycarbonyl)amino-2-methanesulfonyloxy-4-phenylbutyric acid methyl ester (diastereomer mixture) into threo-3-amino-2-hydroxy-4-phenylbutyric acid The ethyl acetate solution (826 mg) of the diastereomer mixture of 3-(ethoxycarbonyl)amino-2-methanesulfonyloxy-4-phenylbutyric acid methyl ester obtained in Example 7 [corresponding to 3-(ethoxycarbonyl)amino-2-methanesulfonyloxy-4-phenylbutyric acid methyl ester (150 mg), calculated as an erythro-isomer; HPLC area ratio of erythro-isomer/threo-isomer=83/17] was solvent-replaced with toluene to obtain a toluene solution (890 mg). N,N-Dimethyl formamide (1 ml) was added to the solution, and the mixture was reacted at 80° C. for 20 hours. HPLC analysis (area percent method) confirmed that the conversion ratio of erythro-3-(ethoxycarbonyl)amino-2-methanesulfonyloxy-4-phenylbutyric acid methyl ester was 98% and the remaining ratio of threo-3-(ethoxycarbonyl)amino-2-methanesulfonyloxy-4-phenylbutyric acid methyl ester was 99%.

The reaction solution thus obtained was concentrated under reduced pressure, and water (1 ml) and 1,4-dioxane (2 ml) were added to the resultant residue to obtain a homogeneous solution. To the solution, a 30% aqueous solution of sodium hydroxide (596 mg) was added, and the mixture was reacted at 80° C. for 12 hours. Determination by HPLC revealed that the amount of threo-3-amino-2-hydroxy-4-phenylbutyric acid in the resultant reaction solution was 75 mg. Also, the HPLC area ratio of threo-isomer/erythro-isomer was 93/7, and the diastereomer excess was 87% d.e.

Example 10

Conversion of 3-(ethoxycarbonyl)amino-2-methanesulfonyloxy-4-phenylbutyric acid methyl ester (diastereomer mixture) into threo-3-amino-2-hydroxy-4-phenylbutyric acid The ethyl acetate solution (825 mg) of the diastereomer mixture of 3-(ethoxycarbonyl)amino-2-methanesulfonyloxy-4-phenylbutyric acid methyl ester obtained in Example 7 [corresponding to 3-(ethoxycarbonyl)amino-2-methanesulfonyloxy-4-phenylbutyric acid methyl ester (150 mg), calculated as an erythro-isomer; HPLC area ratio of erythro-isomer/threo-isomer=83/17] was solvent-replaced with toluene to obtain a toluene solution (1.51 g). N,N-Dimethyl formamide (76 mg) was added to the solution, and the mixture was reacted at 100° C. for 20 hours. HPLC analysis (area percent method) confirmed that the conversion ratio of erythro-3-(ethoxycarbonyl)amino-2-methanesulfonyloxy-4-phenylbutyric acid methyl ester was 98% and the remaining ratio of threo-3-(ethoxycarbonyl)amino-2-methanesulfonyloxy-4-phenylbutyric acid methyl ester was 99%.

The reaction solution thus obtained was concentrated under reduced pressure, and water was added to the resultant residue (329 mg) to obtain an aqueous solution (1.51 g). To the solution, a 30% aqueous solution of sodium hydroxide (672 mg) was added, and the mixture was reacted at 60° C. for 12 hours. Determination by HPLC revealed that the amount of threo-3-amino-2-hydroxy-4-phenylbutyric acid in the resultant reaction solution was 74 mg. Also, the HPLC area ratio of threo-isomer/erythro-isomer was 93/7, and the diastereomer excess was 87% d.e.

Example 11

Conversion of 3-(ethoxycarbonyl)amino-2-methanesulfonyloxy-4-phenylbutyric acid methyl ester (diastereomer mixture) into threo-3-amino-2-hydroxy-4-phenylbutyric acid The ethyl acetate solution (831 mg) of the diastereomer mixture of 3-(ethoxycarbonyl)amino-2-methanesulfonyloxy-4-phenylbutyric acid methyl ester obtained in Example 7 [corresponding to 3-(ethoxycarbonyl)amino-2-methanesulfonyloxy-4-phenylbutyric acid methyl ester (151 mg), calculated as an erythro-isomer; HPLC area ratio of erythro-isomer/threo-isomer=83/17] was solvent-replaced with toluene to obtain a toluene solution (901 mg). Pyridine (1.69 g) was added to the solution, and the mixture was reacted at 100° C. for 18 hours. HPLC analysis (area percent method) confirmed that the conversion ratio of erythro-3-(ethoxycarbonyl)amino-2-methanesulfonyloxy-4-phenylbutyric acid methyl ester was 98% and the remaining ratio of threo-3-

(ethoxycarbonyl)amino-2-methanesulfonyloxy-4-phenylbutyric acid methyl ester was 99%.

The reaction solution thus obtained was concentrated under reduced pressure, and water was added to the resultant residue (327 mg) to obtain an aqueous solution (1.52 g). To the solution, a 30% aqueous solution of sodium hydroxide (665 mg) was added, and the mixture was reacted at 60° C. for 12 hours. Determination by HPLC revealed that the amount of threo-3-amino-2-hydroxy-4-phenylbutyric acid in the resultant reaction solution was 74 mg. Also, the HPLC area ratio of threo-isomer/erythro-isomer was 93/7, and the diastereomer excess was 87% d.e.

Example 12

Crystallization example of threo-3-amino-2-hydroxy-4-phenylbutyric acid

The ethyl acetate solution (8.29 g) of the diastereomer mixture of 3-(ethoxycarbonyl)amino-2-methanesulfonyloxy-4-phenylbutyric acid methyl ester obtained in Example 7 [corresponding to 3-(ethoxycarbonyl)amino-2-methanesulfonyloxy-4-phenylbutyric acid methyl ester (1.50 g), calculated as an erythro-isomer; HPLC area ratio of erythro-isomer/threo-isomer=83/17] was treated in the same manner as that in Example 5. The resultant 4-benzyl-2-oxazolidinone-5-carboxylic acid methyl ester (1.00 g) was mixed with water (10 ml), lithium hydroxide monohydrate (757 mg) was added to the mixture, and the mixture was reacted at 60° C. for 20 hours. The resultant reaction solution was filtrated with a filter to remove insoluble matters, and the filter was then washed with water (1 ml) to obtain a filtrate (12.49 g) free from the insoluble matters. The amount of 3-amino-2-hydroxy-4-phenylbutyric acid in the resultant filtrate was 695 mg calculated as a threo-isomer. Also, the HPLC area ratio of threo-isomer/erythro-isomer was 83/17, and the diastereomer excess was 66% d.e.

To the filtrate thus obtained, conc. hydrochloric acid was added slowly, and the pH was adjusted to pH 4.6 to precipitate crystals. Acetone (12 ml) was added to the solution over 1 hour, the mixture was stirred for further 3 hours under ice-cooling to mature the precipitation of the crystals well, and the precipitated crystals were then filtrated. The resultant wet crystals were washed with acetone (3 ml) and then dried in vacuo to obtain white crystals (564 mg). The purity of threo-3-amino-2-hydroxy-4-phenylbutyric acid was 96% by weight, and the water content was 2% by weight (crystallization yield 94%). Also, the HPLC area ratio of threo-isomer/erythro-isomer was 99/1, and the diastereomer excess was 98% d.e.

Example 13

Crystallization example of threo-3-amino-2-hydroxy-4-phenylbutyric acid

The ethyl acetate solution (8.35 g) of the diastereomer mixture of 3-(ethoxycarbonyl)amino-2-methanesulfonyloxy-4-phenylbutyric acid methyl ester obtained in Example 7 [corresponding to 3-(ethoxycarbonyl)amino-2-methanesulfonyloxy-4-phenylbutyric acid methyl ester (1.51 g), calculated as an erythro-isomer; HPLC area ratio of erythro-isomer/threo-isomer=83/17] was solvent-replaced with toluene to obtain a toluene solution (8.95 g). N,N-Dimethyl formamide (10 ml) was added to the solution, and the mixture was reacted at 80° C. for 20 hours. HPLC analysis (area percent method) confirmed that the conversion ratio of erythro-3-(ethoxycarbonyl)amino-2-methanesulfonyloxy-4-phenylbutyric acid methyl ester was 99% and the remaining ratio of threo-3-(ethoxycarbonyl)amino-2-methanesulfonyloxy-4-phenylbutyric acid methyl ester was 99%.

The reaction solution thus obtained was mixed with water (10 ml), and the mixture was concentrated under reduced pressure. Lithium hydroxide monohydrate (761 mg) was added to the resultant residue (1.03 g), and the mixture was reacted at 60° C. for 20 hours. The amount of 3-amino-2-hydroxy-4-phenylbutyric acid in the resultant reaction solution was 772 mg calculated as a threo-isomer. Also, the HPLC area ratio of threo-isomer/erythro-isomer was 94/6, and the diastereomer excess was 88% d.e.

To the reaction solution thus obtained, conc. hydrochloric acid was added slowly, and the pH was adjusted to pH 4.5 to precipitate crystals. Conc. hydrochloric acid was further added slowly to the mixture, and the pH was adjusted to pH 2 to dissolve most of the precipitated crystals. The solution was filtrated with a filter to remove insoluble matters, and the filter was further washed with water (1 ml) to obtain a light brown filtrate (12.49 g) free from the insoluble matters. The resultant filtrate was then washed with toluene (10 ml), whereby it was possible to transfer most of colored components to the toluene phase. To the solution thus obtained, 4 mol/l of an aqueous lithium hydroxide solution (0.5 ml) was added slowly, and the pH was adjusted to pH 4.8 to precipitate crystals. Acetone (20 ml) was added to the solution over 1 hour, and the mixture was stirred for further 3 hours under ice-cooling to mature the precipitation of the crystals well, and the precipitated crystals were then filtrated. The resultant wet crystals were washed with acetone (3 ml) and then dried in vacuo to obtain white crystals (663 mg). The purity of threo-3-amino-2-hydroxy-4-phenylbutyric acid was 98% by weight, and the water content was 1% by weight (crystallization yield 90%). Also, erythro-3-amino-2-hydroxy-4-phenylbutyric acid was not detected.

$^1$H-NMR Spectra ($D_2O$, sodium 2,2-dimethyl-2-silapentane-5-sulfonate (DSS) internal standard) of the resultant crystals of threo-3-amino-2-hydroxy-4-phenylbutyric acid were: δ 2.95 (1H, dd, H-4, J=14 Hz (H-4), J=8.8 Hz (H-3)), 3.16 (1H, dd, H-4, J=14 Hz (H-4), J=6.8 Hz (H-3)), 3.76–3.83 (1H, m, H-3), 4.06 (1H, d, H-2, J=2.8 Hz (H-3)), 7.35–7.48 (5H, m, Ph).

Also, $^{13}$C NMR spectra ($D_2O$, DSS internal standard) were: δ 38.2, 58.2, 73.4, 130.5, 132.0, 132.3, 138.4, 179.9.

Example 14

Conversion of (2S,3S)-3-(ethoxycarbonyl)amino-2-methanesulfonyloxy-4-phenylbutyric acid methyl ester into (4S,5R)-4-benzyl-2-oxazolidinone-5-carboxylic acid methyl ester (coexistence of acid)

(2S,3S)-3-(Ethoxycarbonyl)amino-2-methanesulfonyloxy-4-phenylbutyric acid methyl ester obtained in Example 4 (HPLC area ratio of erythro-isomer/threo-isomer=99/1) (150 mg) was suspended in toluene (1.5 ml), methanesulfonic acid (45 mg) was added to the suspension, and the mixture was reacted at 100° C. with stirring. The crystals dissolved with the progress of the reaction, and the reaction solution became a homogeneous solution. After reacting for 8 hours, a portion of the reaction solution was sampled and applied to HPLC analysis which revealed that the conversion ratio of (2S,3S)-3-(ethoxycarbonyl)amino-2-methanesulfonyloxy-4-phenylbutyric acid methyl ester was 99% (area percent method).

Example 15

Conversion of (2S,3S)-3-(ethoxycarbonyl)amino-2-methanesulfonyloxy-4-phenylbutyric acid methyl ester into (4S,5R)-4-benzyl-2-oxazolidinone-5-carboxylic acid methyl ester (without reaction accelerator)

(2S,3S)-3-(Ethoxycarbonyl)amino-2-methanesulfonyloxy-4-phenylbutyric acid methyl ester obtained in Example 4 (HPLC area ratio of erythro-isomer/threo-isomer=99/1) (150 mg) was suspended in toluene (1.5 ml), and the suspension was reacted at 100° C. with stirring. The crystals dissolved with the progress of the reaction, and the reaction solution became a homogeneous solution. After reacting for 8 hours, a portion of the reaction solution was sampled and applied to HPLC analysis which revealed that the conversion ratio of (2S,3S)-3-(ethoxycarbonyl)amino-2-methanesulfonyloxy-4-phenylbutyric acid methyl ester was 62% (area percent method). After further reacting at 110° C. for 20 hours, a portion of the reaction solution was sampled and applied to HPLC analysis which revealed that the conversion ratio of (2S,3S)-3-(ethoxycarbonyl)amino-2-methanesulfonyloxy-4-phenylbutyric acid methyl ester was 99% (area percent method).

From the results of Example 14 and Example 15, it is apparent that methanesulfonic acid is effective as a reaction accelerator.

Example 16

Conversion of (2S,3S)-3-(ethoxycarbonyl)amino-2-hydroxy-4-phenylbutyric acid into (4S,5R)-4-benzyl-2-oxazolidinone-5-carboxylic acid methyl ester (2S,3S)-3-(Ethoxycarbonyl)amino-2-hydroxy-4-phenylbutyric acid obtained in Example 1 (HPLC area ratio of erythro-isomer/threo-isomer=99/1) (66.87 g) was dissolved in methanol (340 ml) and toluene (300 ml), methanesulfonic acid (2.41 g) was added to the mixture, and the mixture was reacted under reflux for 5 hours. After cooling the resultant reaction solution to room temperature, the pH of the solution was adjusted to pH 6 with a 5% aqueous solution of sodium hydrogencarbonate (42.04 g), and methanol was distilled off under reduced pressure. Ethyl acetate (360 ml) and water (130 ml) were added to the resultant concentrate (330.6 g), the pH was adjusted to pH 8 with a 5% aqueous solution of sodium hydrogencarbonate (12.51 g), and the aqueous phase was separated. The resultant organic phase was then washed with water (130 ml) and concentrated under reduced pressure to obtain an ethyl acetate extract (462.7 g). Determination by HPLC revealed that the amount of (2S,3S)-3-(ethoxycarbonyl)amino-2-hydroxy-4-phenylbutyric acid methyl ester in the resultant extract was 68.27 g. Also, the HPLC area ratio of erythro-isomer/threo-isomer was 99/1, and the diastereomer excess was 98% d.e.

To the ethyl acetate extract (450.3 g) thus obtained [containing (2S,3S)-3-(ethoxycarbonyl)amino-2-hydroxy-4-phenylbutyric acid (66.44 g)], triethylamine (33.46 g) was added under ice-cooling, methanesulfonyl chloride (32.46 g) was then added over 2 hours, and the mixture was reacted at the same temperature for 1 hour. Water (660 ml) was added to the resultant reaction solution, and the aqueous phase was separated. The resultant organic phase was then washed with water (330 ml), ethyl acetate was distilled off under reduced pressure, and solvent-replacement was carried out with toluene. The resultant solvent-replaced solution was reacted at 110° C. for 12 hours to obtain a toluene solution (668.5 g). Determination by HPLC revealed that the amount of (4S,5R)-4-benzyl-2-oxazolidinone-5-carboxylic acid methyl ester in the resultant toluene solution was 54.39 g. Also, the HPLC area ratio of erythro-isomer/threo-isomer was 99/1, and the diastereomer excess was 98% d.e.

Example 17

Conversion of (2S,3S)-3-(ethoxycarbonyl)amino-2-methanesulfonyloxy-4-phenylbutyric acid methyl ester into (2R,3S)-3-amino-2-hydroxy-4-phenylbutyric acid via inversion reaction in the coexistence of water To the ethyl acetate extract (10.17 g) of (2S,3S)-3-(ethoxycarbonyl)amino-2-hydroxy-4-phenylbutyric acid methyl ester obtained in Example 16 [containing (2S,3S)-3-(ethoxycarbonyl)amino-2-hydroxy-4-phenylbutyric acid methyl ester (1.50 g); HPLC area ratio of erythro-isomer/threo-isomer=99/1], triethylamine (756 mg) was added under ice-cooling, methanesulfonyl chloride (733 mg) was then added over 10 minutes, and the mixture was reacted at the same temperature for 2 hours. Water (15 ml) was added to the resultant reaction solution, and the aqueous phase was separated. The resultant organic phase was then washed with water (8 ml), ethyl acetate was distilled off under reduced pressure, and solvent-replacement was carried out with toluene to obtain a solvent-replaced solution (7.59 g). Water (1.5 ml) and N,N-dimethyl formamide (5.98 g) were added to the solution (pH 9). The mixture was reacted at 85° C. for 12 hours. The pH of the resultant reaction solution (14.88 g) was pH 4. Determination by HPLC of the reaction solution thus obtained revealed that the amount of (4S,5R)-4-benzyl-2-oxazolidinone-5-carboxylic acid methyl ester in reaction solution was 0.35 g and that of (2R,3S)-3-(ethoxycarbonyl)amino-2-hydroxy-4-phenylbutyric acid methyl ester was 1.04 g. When combining these two inversion products, the HPLC area ratio of threo-isomer/erythro-isomer was 99/1, and the diastereomer excess was 98% d.e.

The reaction solution (14.05 g) thus obtained [containing (4S,5R)-4-benzyl-2-oxazolidinone-5-carboxylic acid methyl ester (0.33 g) and (2R,3S)-3-(ethoxycarbonyl)amino-2-hydroxy-4-phenylbutyric acid methyl ester (0.98 g)] was solvent-replaced with toluene under reduced pressure, and insoluble matters were filtered off. Water (5 ml) and a 30% aqueous solution of sodium hydroxide (6.61 g) were added to the resultant toluene solution, and the mixture was reacted at 60° C. for 12 hours with stirring. The organic phase was separated from the resultant reaction solution (pH 14), water (2 ml) was added to the organic phase, and the mixture was throughly mixed at 60° C. with stirring. The resultant aqueous phase was separated and collected together with the previous aqueous phase. Determination by HPLC of the aqueous phase thus obtained revealed that the content of (2R,3S)-3-amino-2-hydroxy-4-phenylbutyric acid in the aqueous phase was 0.95 g, the yield was 97%, and the purity was 99% (area percent method). Also, the HPLC area ratio of threo-isomer/erythro-isomer was 99/1, and the diastereomer excess was 98% d.e.

Example 18

Conversion of purified (4S,5R)-4-benzyl-2-oxazolidinone-5-carboxylic acid methyl ester into (2R,3S)-3-amino-2-hydroxy-4-phenylbutyric acid The toluene solution (66.9 g) obtained in Example 16 [containing (4S,5R)-4-benzyl-2-oxazolidinone-5-carboxylic acid methyl ester (5.44 g); HPLC area ratio of threo-isomer/erythro-isomer=99/1] was concentrated under reduced pressure to obtain an oily substance (7.79 g). Toluene was added to the oily substance up to the amount of 54.7 g, and the substance was again dissolved by stirring at 70° C. for 3 hours. When the toluene solution was cooled and then stirred for 3 days, it was found that crystals precipitated from the solution. The solution was further cooled to −10° C., and precipitated crystals were separated by suction filtration. The crystals were washed with cold toluene (150 ml) and then dried in vacuo to obtain purified (4S,5R)-4-benzyl-2-oxazolidinone-5-carboxylic acid methyl ester (5.06 g) as white crystals. The purity of (4S,5R)-4-benzyl-2-oxazolidinone-5-carboxylic acid methyl ester was 99% (area percent method). Also, the HPLC area ratio of threo-isomer/erythro-isomer was 99/1, and the diastereomer excess was 99% d.e.

$^1$H-NMR Spectra (CDCl$_3$, TMS internal standard) of the resultant (4S,5R)-4-benzyl-2-oxazolidinone-5-carboxylic acid methyl ester were: δ 2.79 (1H, dd, CH$_2$Ph, J=13.2 Hz (CH$_2$Ph), 10 Hz (H-4)), 3.07 (1H, dd, CH$_2$Ph, J=13.2 Hz (CH$_2$Ph), 4.4 Hz (H-4)), 3.86 (3H, s, CO$_2$CH$_3$), 4.01–4.09 (1H, m, H-4), 4.72 (1H, d, H-5, J=4.4 Hz (H-4)), 7.15–7.38 (5H, m, Ph).

On the other hand, the crystallization mother liquor and the toluene washing were combined, the solution was then concentrated under reduced pressure to remove toluene, and the residue was further dried in vacuo to obtain methanesulfonic acid ethyl ester (2.69 g) as an oily substance.

$^1$H-NMR Spectra (CDCl$_3$, TMS internal standard) of the resultant methanesulfonic acid ethyl ester were: δ 0.92 (3H, t, CH$_3$, J=6.8 Hz), 2.23 (3H, s, CH$_3$SO$_2$), 3.77 (2H, q, CH$_2$, J=6.8 Hz).

Purified (4S,5R)-4-benzyl-2-oxazolidinone-5-carboxylic acid methyl ester (2.35 g) obtained as described above was suspended in toluene (25 ml) and water (10 ml), a 30% aqueous solution of sodium hydroxide (13.33 g) was added to the suspension, and the mixture was reacted at 60° C. for 12 hours with stirring. Determination by HPLC of the resultant reaction solution revealed that the content of (2R,3S)-3-amino-2-hydroxy-4-phenylbutyric acid in the reaction solution was 1.91 g, the yield was 98%, and the purity was 98% (area percent method). Also, the HPLC area ratio of threo-isomer/erythro-isomer was 99/1, and the diastereomer excess was 99% d.e.

Comparative Example 1

Conversion of (4S,5R)-4-benzyl-2-oxazolidinone-5-carboxylic acid methyl ester into (2R,3S)-3-amino-2-hydroxy-4-phenylbutyric acid (without water treatment)

Firstly, a 30% aqueous solution of sodium hydroxide (13.33 g) was cooled to 5° C. with stirring, and the toluene solution (28.88 g) obtained in Example 16 [containing (4S,5R)-4-benzyl-2-oxazolidinone-5-carboxylic acid methyl ester (2.35 g); HPLC area ratio of threo-isomer/erythro-isomer=99/1] was added dropwise to the cooled solution over 30 minutes (pH 14). The temperature of the mixture was raised to 60° C., and the mixture was reacted for further 12 hours with stirring. Water (10 ml) was then added to the reaction solution, and the organic phase was separated from the resultant reaction solution. Water (4 ml) was added to the organic phase, and the mixture was throughly mixed at 60° C. with stirring. The aqueous phase was separated and collected together with the previous aqueous phase. Determination by HPLC of the aqueous phase (27.98 g) thus obtained revealed that the content of (2R,3S)-3-amino-2-hydroxy-4-phenylbutyric acid in the aqueous phase was 1.24 g, the yield was 64%, and the purity was 64% (area percent method). Also, the HPLC area ratio of erythro-isomer/threo-isomer was 99/1, the diastereomer excess was 98% d.e., and the content of (2R,3S)-3-ethylamino-2-hydroxy-4-phenylbutyric acid secondarily produced was 35% (area percent method).

Example 19

Conversion of (4S,5R)-4-benzyl-2-oxazolidinone-5-carboxylic acid methyl ester into (2R,3S)-3-amino-2-hydroxy-4-phenylbutyric acid (with water treatment)

The toluene solution (28.88 g) obtained in Example 16 [containing (4S,5R)-4-benzyl-2-oxazolidinone-5-carboxylic acid methyl ester (2.35 g); HPLC area ratio of threo-isomer/erythro-isomer=99/1] was mixed with water (10 ml), and the mixture was reacted at 80° C. for 12 hours with stirring (pH 1). To the mixture, a 30% aqueous solution of sodium hydroxide (13.33 g) was added, and the mixture was reacted at 60° C. for 12 hours with stirring. The organic phase was separated from the resultant reaction solution, and water (5 ml) was added to the organic phase. The mixture was throughly mixed at 60° C. with stirring. The resultant aqueous phase was separated and collected together with the previous aqueous phase. Determination by HPLC of the aqueous phase thus obtained revealed that the content of (2R,3S)-3-amino-2-hydroxy-4-phenylbutyric acid in the aqueous phase was 1.92 g, the yield was 98%, and the purity was 99% (area percent method). Also, the HPLC area ratio of threo-isomer/erythro-isomer was 99/1, and the diastereomer excess was 99% d.e.

Example 20

Conversion of (4S,5R)-4-benzyl-2-oxazolidinone-5-carboxylic acid methyl ester into (2R,3S)-3-amino-2-hydroxy-4-phenylbutyric acid (with water treatment)

The toluene solution (92.42 g) obtained in Example 16 [containing (4S,5R)-4-benzyl-2-oxazolidinone-5-carboxylic acid methyl ester (7.52 g); HPLC area ratio of threo-isomer/erythro-isomer=99/1] was concentrated and solvent-replaced with 1,4-dioxane to obtain a 1,4-dioxane solution (92.50 g).

The 1,4-dioxane solution (28.89 g) thus obtained [containing (4S,5R)-4-benzyl-2-oxazolidinone-5-carboxylic acid methyl ester (2.35 g); HPLC area ratio of threo-isomer/erythro-isomer=99/1] was mixed with water (10 ml), and the mixture was reacted at 60° C. for 60 hours with stirring (pH 1). To the mixture, a 30% aqueous solution of sodium hydroxide (13.33 g) was added, and the mixture was reacted at 60° C. for 12 hours with stirring. Water (15 ml) was added to the reaction solution separated into two layers to homogenize the solution. Determination by HPLC of the solution revealed that the content of (2R,3S)-3-amino-2-hydroxy-4-phenylbutyric acid was 1.92 g, the yield was 98%, and the purity was 99% (area percent method) Also, the HPLC area ratio of threo-isomer/erythro-isomer was 99/1, and the diastereomer excess was 99% d.e.

Comparative Example 2

Conversion of (4S,5R)-4-benzyl-2-oxazolidinone-5-carboxylic acid methyl ester into (2R,3S)-3-amino-2-hydroxy-4-phenylbutyric acid (without treatment)

The toluene solution (28.88 g) obtained in Example 16 [containing (4S,5R)-4-benzyl-2-oxazolidinone-5-carboxylic acid methyl ester (2.35 g); HPLC area ratio of threo-isomer/erythro-isomer=99/1] was mixed with water (10 ml), a 30% aqueous solution of sodium hydroxide (13.33 g) was added to the mixture (pH 14), and the mixture was reacted at 60° C. for 12 hours with stirring. The organic phase was separated from the reaction solution, water (4 ml) was added to the organic phase, and the mixture was throughly mixed at 60° C. with stirring. The aqueous phase was separated and collected together with the previous aqueous phase. Determination by HPLC of the aqueous phase thus obtained revealed that the content of (2R,3S)-3-amino-2-hydroxy-4-phenylbutyric acid in the aqueous phase was 1.56 g, the yield was 80%, and the purity was 79% (area percent method). Also, the HPLC area ratio of threo-isomer/erythro-isomer was 99/1, the diastereomer excess was 98% d.e., and the content of (2R,3S)-3-ethylamino-2-hydroxy-4-phenylbutyric acid secondarily prodeced was 18% (area percent method).

From the results of Example 19, Example 20 and Comparative example 2, it is apparent that water treatment increases the yield and the purity.

Example 21

Crystallization example of (2R,3S)-3-amino-2-hydroxy-4-phenylbutyric acid

Conc. hydrochloric acid was added in portions at 60° C. to the aqueous phase (29.97 g) obtained in Example 19 [containing (2R,3S)-3-amino-2-hydroxy-4-phenylbutyric acid (1.85 g); HPLC area ratio of threo-isomer/erythro-isomer=99/1], whereby crystals gradually precipitated. The pH was finally adjusted to pH 5. Then, cooling crystallization was carried out at a cooling rate of 5° C./hour, and precipitated crystals were separated by suction filtration. The crystals were washed with cold water (8 ml) and then dried in vacuo to obtain white crystals (1.77 g). The purity of (2R,3S)-3-amino-2-hydroxy-4-phenylbutyric acid was 98% by weight, and the water content was 2% by weight. Neither erythro-isomer (diastereomer) nor (2S,3R)-isomer (enantiomer) was detected.

$^1$H-NMR Spectra (D$_2$O, sodium 2,2-dimethyl-2-silapentane-5-sulfonate (DSS) internal standard) of the resultant crystals of (2R,3S)-3-amino-2-hydroxy-4-phenylbutyric acid were: δ 2.95 (1H, dd, H-4, J=14 Hz (H-4), J=8.8 Hz (H-3)), 3.16 (1H, dd, H-4, J=14 Hz (H-4), J=6.8 Hz (H-3)), 3.76–3.83 (1H, m, H-3), 4.06 (1H, d, H-2, J=2.8 Hz (H-3)), 7.35–7.48 (5H, m, Ph).

Also, $^{13}$C NMR spectra (D$_2$O, DSS internal standard) were: δ 38.2, 58.2, 73.4, 130.5, 132.0, 132.3, 138.4, 179.9.

Reference Example 1

Conversion of (4S,5R)-4-benzyl-2-oxazolidinone-5-carboxylic acid methyl ester into (2R,3S)-3-ethylamino-2-hydroxy-4-phenylbutyric acid From the toluene solution (88.73 g) obtained in Example 16 [containing (4S,5R)-4-benzyl-2-oxazolidinone-5-carboxylic acid methyl ester (7.22 g) and methanesulfonic acid ethyl ester; HPLC area ratio of threo-isomer/erythro-isomer=99/1], toluene was distilled off under reduced pressure, and tetrahydrofuran was then added to the residue to obtain a solvent-replaced solution (90.11 g). The solvent-replaced solution was added dropwise to a suspension of sodium hydride (oily, 60% by weight) (1.48 g) and tetrahydrofuran (15 ml) cooled to 5° C. over 15 minutes. THF (30 ml) was further added to the mixture, and the mixture was reacted at the same temperature for 1 hour. Then, the reaction solution was decanted to remove most of a large quantity of white precipitates. The resultant supernatant solution was further filtrated to remove insoluble matters, the solvent of the filtrate was distilled off under reduced pressure, and the residue was dried in vacuo to obtain an oily substance (3.94 g).

Water (30 ml) and a 30% aqueous solution of sodium hydroxide (30.42 g) were added to the oily substance (3.35 g) thus obtained, and the mixture was reacted at 60° C. for 20 hours. To the resultant reaction solution [containing (2R,3S)-3-amino-2-hydroxy-4-phenylbutyric acid (17%), (2S,3S)-3-amino-2-hydroxy-4-phenylbutyric acid (1%), and secondarily produced (2R,3S)-3-ethylamino-2-hydroxy-4-phenylbutyric acid (76%) (all values by area percent method)], conc. hydrochloric acid was added in portions at 60° C., whereby crystals gradually precipitated. The pH was finally adjusted to pH 5. Then, cooling crystallization was carried out at a cooling rate of 5° C./hour, and precipitated crystals were separated by suction filtration. The crystals were washed with cold water (4 ml) and then dried in vacuo to obtain white crystals (1.18 g). The content of (2R,3S)-3-ethylamino-2-hydroxy-4-phenylbutyric acid was 97% (area percent method).

$^1$H NMR Spectra (D$_2$O—K$_2$CO$_3$, sodium 2,2-dimethyl-2-silapentane-5-sulfonate (DSS) internal standard) of the resultant (2R,3S)-3-ethylamino-2-hydroxy-4-phenylbutyric acid were: δ 1.03 (3H, t, CH$_3$, J=7.1 Hz), 2.63–2.74 (2H, m, CH$_2$), 2.83 (1H, dd, H-4, J=14 Hz (H-4), J=8.8 Hz (H-3)), 2.92 (1H, dd, H-4, J=14 Hz (H-4), J=6.4 Hz (H-3)), 3.35 (1H, m, H-3), 3.85 (1H, d, H-2, J=2.0 Hz (H-3)), 7.30–7.44 (5H, m, Ph).

Also, $^{13}$C NMR spectra (D$_2$O—K$_2$CO$_3$, DSS internal standard) were: δ 16.1, 40.3, 44.0, 63.6, 74.1, 129.5, 131.6, 132.3, 141.6, 167.4.

Reference Example 2

Crystallization example of a mixture of (2R,3S)-3-amino-2-hydroxy-4-phenylbutyric acid and (2R,3S)-3-ethylamino-2-hydroxy-4-phenylbutyric acid To the aqueous phase (25.50 g) obtained in Comparative example 1 [containing (2R,3S)-3-amino-2-hydroxy-4-phenylbutyric acid (1.13 g); HPLC area ratio of threo-isomer/erythro-isomer=99/1; containing secondarily produced (2R,3S)-3-ethylamino-2-hydroxy-4-phenylbutyric acid (35%) (area percent method)], water (75 ml) was added and conc. hydrochloric acid was added in portions at 60° C., whereby crystals gradually precipitated. The pH was finally adjusted to pH 5. Then, cooling crystallization was carried out at a cooling rate of 5° C./hour, and precipitated crystals were separated by suction filtration. The crystals were washed with cold water (4 ml) and then dried in vacuo to obtain white crystals (1.07 g). The content of (2R,3S)-3-ethylamino-2-hydroxy-4-phenylbutyric acid was 72% (area percent method).

Signals characteristic of (2R,3S)-3-ethylamino-2-hydroxy-4-phenylbutyric acid as shown in Reference example 1 were confirmed in $^1$H-NMR spectra ($D_2O$—$K_2CO_3$, sodium 2,2-dimethyl-2-silapentane-5-sulfonate (DSS) internal standard) of the resultant crystals.

INDUSTRIAL UTILIZATION

According to the present invention, it is possible to prepare conveniently and efficiently, and with industrial advantages, 3-amino-2-hydroxypropionic acid derivatives (1) having a particular steric configuration from N-protected-3-amino-2-hydroxypropionic acid derivatives (2) having a reverse steric configuration at 2-position carbon.

The invention claimed is:

1. A process for preparing a 3-amino-2-hydroxypropionic acid derivative represented by the general formula (1):

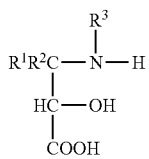

(1)

wherein $R^1$, $R^2$ and $R^3$, independently from each other, represent a hydrogen atom, a substituted or unsubstituted alkyl group having 1 to 30 carbon atoms, a substituted or unsubstituted aryl group having 6 to 30 carbon atoms, or a substituted or unsubstituted aralkyl group having 7 to 30 carbon atoms, which comprises the steps of:

converting a N-protected-3-amino-2-hydroxypropionic acid derivative having a steric configuration at 2-position carbon reverse to that of the above compound (1) and represented by the general formula (2):

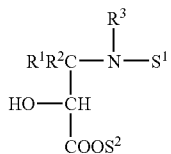

(2)

wherein $R^1$, $R^2$ and $R^3$ are as defined above;

$S^1$ represents an urethane-type protecting group for an amino group represented by —$COOR^4$, wherein $R^4$ represents a substituted or unsubstituted alkyl group having 1 to 30 carbon atoms, a substituted or unsubstituted aryl group having 6 to 30 carbon atoms, or a substituted or unsubstituted aralkyl group having 7 to 30 carbon atoms; and $S^2$ represents a hydrogen atom or an ester residue;

by a reaction for introducing a leaving group, into a N-protected-3-aminopropionic acid derivative represented by the general formula (3):

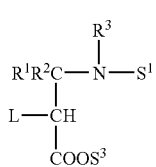

(3)

wherein $R^1$, $R^2$ and $R^3$ and $S^1$ are as defined above;

L represents a leaving group selected from the group consisting of a sulfonyloxy group, a halosulfinyloxy group and a halogen atom; and $S^3$ represents a hydrogen atom or an ester residue;

then converting the derivative (3), by a reaction for inverting the steric configuration at 2-position, into a substituted-3-amino-2-hydroxypropionic acid derivative having an inverted steric configuration at 2-position carbon and represented by the general formula (4):

(4)

wherein $R^1$, $R^2$ and $R^3$ are as defined above;

$S^4$ represents a hydrogen atom or an ester residue;

$S^5$ represents a hydrogen atom or a substituent derived from $S^1$;

$S^6$ represents $S^1$ when $S^5$ is a hydrogen atom, or a substituent derived from $S^1$, taken together with $S^5$, when $S^5$ is a substituent derived from $S^1$; and $S^1$ is as defined above;

and then converting the derivative (4), by a reaction for removing substituents $S^4$, $S^5$ and $S^6$, into 3-amino-2-hydroxypropionic acid derivative (1).

2. The process according to claim 1 wherein leaving group L is a sulfonyloxy group.

3. The process according to claim 1 wherein leaving group L is a halosulfinyloxy group or a halogen atom.

4. The process according to claim 2 wherein $S^2$ is an ester residue.

5. The process according to claim 3 wherein $S^2$ is a hydrogen atom.

6. The process according to claim 1 wherein $S^3$ and $S^4$ are the same group as $S^2$.

7. The process according to claim 1 wherein substituted-3-amino-2-hydroxypropionic acid derivative (4) contains at least one of derivatives represented by the general formulae (4a), (4b) and (4c):

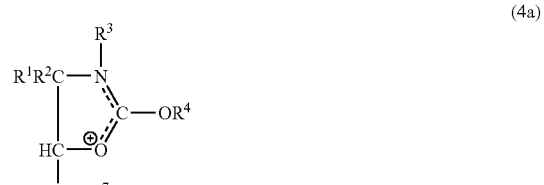

(4a)

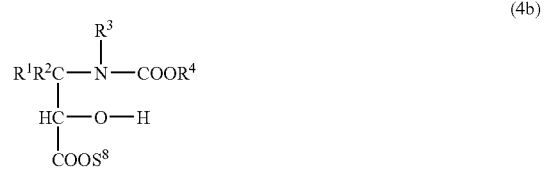

(4b)

-continued

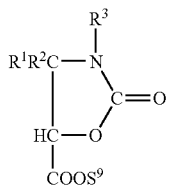
(4c)

wherein $R^1$, $R^2$, $R^3$ and $R^4$ are as defined above;
and $S^7$, $S^8$ and $S^9$ are a hydrogen atom or an ester residue.

8. The process according to claim 1 wherein $R^1$ and $R^2$ are different from each other.

9. The process according to claim 1 wherein N-protected-3-aminopropionic acid derivative (3) is a derivative having $R^1$ and $R^2$ different from each other and is a mixture of diastereomers having the same steric configuration at 3-position carbon and having a different steric configuration only at 2-position carbon, and one of the diastereomers is selectively converted into substituted-3-amino-2-hydroxy-propionic acid derivative (4).

10. The process according to claim 1 wherein N-protected-3-aminopropionic acid derivative (3) is a derivative having $R^1$ and $R^2$ different from each other and is a mixture of diastereomers having the same steric configuration at 3-position carbon and having a different steric configuration only at 2-position carbon; one of the diastereomers is selectively converted into substituted-3-amino-2-hydroxypropionic acid derivative (4); and the resultant substituted-3-amino-2-hydroxypropionic acid derivative (4) and other diastereomer of N-protected-3-aminopropionic acid derivative (3) remaining are then hydrolyzed together to obtain 3-amino-2-hydroxypropionic acid derivative (1) having diastereomer excess higher than that of N-protected-3-aminopropionic acid derivative (3).

11. The process according to claim 9 wherein leaving group L is a sulfonyloxy group.

12. The process according to claim 9 wherein $S^2$ is an ester residue.

13. The process according to claim 9 wherein $S^3$ and $S^4$ are the same group as $S^2$.

14. The process according to claim 1 wherein N-protected-3-amino-2-hydroxypropionic acid derivative (2) is treated with a leaving group-introducing agent, in the step of introducing leaving group L into N-protected-3-amino-2-hydroxypropionic acid derivative (2) to convert the derivative into N-protected-3-aminopropionic acid derivative (3).

15. The process according to claim 1 wherein the step of inverting the steric configuration at 2-position carbon of N-protected-3-aminopropionic acid derivative (3) to convert the derivative into substituted-3-amino-2-hydroxypropionic acid derivative (4) is carried out under heating.

16. The process according to claim 1 wherein an acidic substance is used as a reaction accelerator, in the step of inverting the steric configuration at 2-position carbon of N-protected-3-aminopropionic acid derivative (3) to convert the derivative into substituted-3-amino-2-hydroxypropionic acid derivative (4).

17. The process according to claim 1 wherein a weakly basic substance is used as a reaction accelerator, in the step of inverting the steric configuration at 2-position carbon of N-protected-3-aminopropionic acid derivative (3) to convert the derivative into substituted-3-amino-2-hydroxypropionic acid derivative (4).

18. The process according to claim 1 wherein substituted-3-amino-2-hydroxypropionic acid derivative (4) obtained in the step of inverting the steric configuration at 2-position carbon of N-protected-3-aminopropionic acid derivative (3) to convert the derivative into substituted-3-amino-2-hydroxypropionic acid derivative (4), without isolation and/or purification, is contacted with water under acidic to neutral conditions and subjected to heat treatment.

19. The process according to claim 18 wherein the contact with water under acidic to neutral conditions and the heat treatment are carried out simultaneously with the inversion of the steric configuration at 2-position carbon of N-protected-3-aminopropionic acid derivative (3) to convert into substituted-3-amino-2-hydroxypropionic acid derivative (4).

20. The process according to claim 18 wherein the step of contacting with water and subjecting to heat treatment is carried out under heating to above 40° C.

21. The process according to claim 1 wherein substituted-3-amino-2-hydroxypropionic acid derivative (4) is isolated and/or purified to a pure form.

22. The process according to claim 21 wherein a 2-oxazolidinone-5-carboxylic acid ester derivative wherein $S^4$ is an ester residue and $S^5$ and $S^6$, taken together, are a carbonyl group is crystallized using an aromatic hydrocarbon, when substituted-3-amino-2-hydroxypropionic acid derivative (4) is isolated and/or purified to a pure form.

23. The process according to claim 1 wherein substituted-3-amino-2-hydroxypropionic acid derivative (4) is hydrolyzed in the step of converting substituted-3-amino-2-hydroxypropionic acid derivative (4) into 3-amino-2-hydroxypropionic acid derivatives (1).

24. The process according to claim 23 wherein the hydrolysis is carried out under basic conditions.

25. The process according to claim 1 wherein N-protected-3-amino-2-hydroxypropionic acid derivative (2) is obtained by hydrolyzing a dihaloketone derivative represented by the general formula (5):

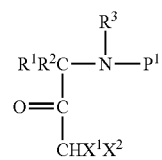
(5)

wherein $R^1$, $R^2$ and $R^3$ are as defined above;
$P^1$ represents a hydrogen atom or a protecting group for an amino group; and
$X^1$ and $X^2$, independently from each other, represent a halogen atom;
to convert into 3-amino-2-hydroxypropionic acid derivative represented by the general formula (6):

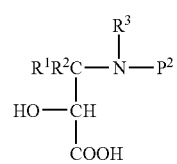
(6)

wherein $R^1$, $R^2$ and $R^3$ are as defined above;
and $P^2$ represents a hydrogen atom or the above $P^1$;

and, if necessary, by further converting $P^1$ or $P^2$ into $S^1$ and/or by further esterifying 3-amino-2-hydroxypropionic acid derivative.

26. The process according to claim 1 wherein $R^1$ is a benzyl group and $R^2$ is a hydrogen atom.

27. The process according to claim 1 wherein $R^3$ is a hydrogen atom.

28. The process according to claim 1 which further comprises the step of crystallizing 3-amino-2-hydroxypropionic acid derivative, by converting an acid or a base coexisting in a solution of 3-amino-2-hydroxypropionic acid derivative (1) obtained as an acidic or basic aqueous solution into a salt soluble in an organic solvent and/or water by neutralization using a base or an acid, whereby precipitating 3-amino-2-hydroxypropionic acid derivative (1) from a medium consisting of water or a mixture of an organic solvent and water, and at the same time, dissolving the above salt formed in said medium.

29. A process for preparing a 3-amino-2-hydroxypropionic acid derivative represented by the general formula (1):

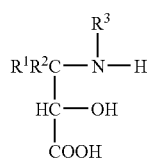
(1)

wherein $R^1$, $R^2$ and $R^3$, independently from each other, represent a hydrogen atom, a substituted or unsubstituted alkyl group having 1 to 30 carbon atoms, a substituted or unsubstituted aryl group having 6 to 30 carbon atoms, or a substituted or unsubstituted aralkyl group having 7 to 30 carbon atoms, which comprises the steps of:

reacting a N-protected-3-amino-2-hydroxypropionic acid derivative having a steric configuration at 2-position carbon reverse to that of the above compound (1) and represented by the general formula (2):

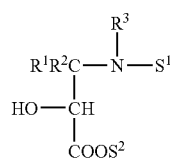
(2)

wherein $R^1$, $R^2$ and $R^3$ are as defined above;
$S^1$ represents an urethane-type protecting group for an amino group represented by —$COOR^4$, wherein $R^4$ represents a substituted or unsubstituted alkyl group having 1 to 30 carbon atoms, a substituted or unsubstituted aryl group having 6 to 30 carbon atoms, or a substituted or unsubstituted aralkyl group having 7 to 30 carbon atoms; and
$S^2$ represents a hydrogen atom or an ester residue;
with a leaving group-introducing agent to convert the derivative (2) into a N-protected-3-aminopropionic acid derivative represented by the general formula (3):

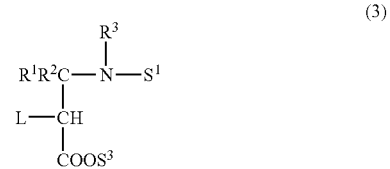
(3)

wherein $R^1$, $R^2$, $R^3$ and $S^1$ are as defined above;
L represents a leaving group selected from the group consisting of a sulfonyloxy group, a halosulfinyloxy group, and a halogen atom; and
$S^3$ represents a hydrogen atom or an ester residue;
then treating the derivative (3) in the presence or absence of an acidic substance or a basic substance to convert the derivative (3) into a substituted-3-amino-2-hydroxypropionic acid derivative having an inverted steric configuration at 2-position carbon and represented by the general formula (4):

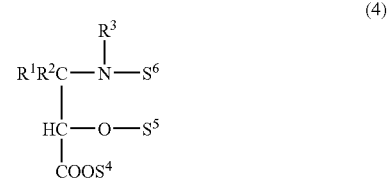
(4)

wherein $R^1$, $R^2$ and $R^3$ are as defined above;
$S^4$ represents a hydrogen atom or an ester residue;
$S^5$ represents a hydrogen atom or a substituent derived from $S^1$;
$S^6$ represents $S^1$ when $S^5$ is a hydrogen atom, or a substituent derived from $S^1$, taken together with $S^5$, when $S^5$ is a substituent derived from $S^1$; and $S^1$ is as defined above;
and then removing substituents $S^4$, $S^5$ and $S^6$ to convert the derivative (4) into 3-amino-2-hydroxypropionic acid derivative (1).

30. The process according to claim 1 wherein the reaction for removing substituents $S^4$, $S^5$ and $S^6$ is carried out by acid treatment, base treatment, hydrolysis, catalytic reduction, electrolytic reduction, or Zn/AcOH treatment.

31. The process according to claim 1 wherein each substituent of the substituted alkyl group, substituted aryl group, and substituted aralkyl group is selected from the group consisting of a chlorine atom, a fluorine atom, and a methoxy group.

32. The process according to claim 1 wherein the alkyl group is selected from the group consisting of a methyl group, an ethyl group, a propyl group, an isopropyl group, an isobutyl group, and a cyclohexylmethyl group; the aryl group is selected from the group consisting of a phenyl group, a p-chlorophenyl group, a p-fluorophenyl group, a methoxyphenyl group, a 1-naphthyl group, and a 2-naphthyl group; and the aralkyl group is selected from the group consisting of a benzyl group, a p-methoxybenzyl group, a 3-phenylpropyl group, and a 2-phenylpropyl group.

33. The process according to claim 1 wherein the ester residue is selected from the group consisting of a lower alkyl group having 1 to 4 carbon atoms and a substituted or unsubstituted benzyl group.

* * * * *